US006975401B2

(12) United States Patent
Tsuchiya

(10) Patent No.: US 6,975,401 B2
(45) Date of Patent: Dec. 13, 2005

(54) METHOD OF CALCULATING OPTICAL PATH DISTRIBUTION INSIDE SCATTERING ABSORBER

(75) Inventor: Yutaka Tsuchiya, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 445 days.

(21) Appl. No.: 10/239,245

(22) PCT Filed: Mar. 6, 2001

(86) PCT No.: PCT/JP01/01724

§ 371 (c)(1),
(2), (4) Date: Sep. 20, 2002

(87) PCT Pub. No.: WO01/71319

PCT Pub. Date: Sep. 27, 2001

(65) Prior Publication Data

US 2003/0078503 A1 Apr. 24, 2003

(30) Foreign Application Priority Data

Mar. 21, 2000 (JP) .......................... 2000-078534

(51) Int. Cl.[7] .......................... G01N 21/00; A61B 6/00
(52) U.S. Cl. ...................... 356/432; 356/338; 600/473
(58) Field of Search ............................ 356/432–436, 356/337–343; 600/473–477; 703/11

(56) References Cited

U.S. PATENT DOCUMENTS 5,678,556 A * 10/1997 Maki et al. .................. 600/477

FOREIGN PATENT DOCUMENTS

| EP | 0 692 708 A2 | 1/1996 |
|----|--------------|--------|
| EP | 0 806 650 A2 | 11/1997 |
| JP | 8-29329 | 2/1996 |
| JP | 9-257694 | 10/1997 |
| JP | 10-318911 | 12/1998 |
| JP | 11-311569 | 11/1999 |
| JP | 11-337476 | 12/1999 |

OTHER PUBLICATIONS

H.L. Graber et al., "Imaging of Multiple Targets in Dense Scattering Media," *SPIE*, vol. 2570, 1995, pp. 219–234.
A. Maki et al., "Reconstructing Absorber Images in a Three–Dimensional Scattering Medium by Using Photon–Path Data," *OSA Tops*, vol. 2, 1996, pp. 299–304.
H. Jiang et al., "Optical Image Reconstruction Using Frequency–Domain Data: Simulations and Experiments," *Journal of the Optical Society of America*, vol. 13, No. 2, Feb. 1996, pp. 253–266.

(Continued)

*Primary Examiner*—Zandra V. Smith
*Assistant Examiner*—Amanda Merlino
(74) *Attorney, Agent, or Firm*—Drinker Biddle & Reath LLP

(57) ABSTRACT

A method comprises a first step of dividing a measured medium into N voxels; a second step of assuming an imaginary medium identical to the measured medium except for absence of absorption; a third step of setting a light injection position and a light detection position for the imaginary medium; a fourth step of calculating an impulse response s(t) at the light detection position; a fifth step of calculating a probability density $U_i(t',t)$ that the impulse response at a time t at the light detection position has existed in voxel i (i=1, ..., N; 1≦N) at a point of time t' (0≦t'≦t); a sixth step of calculating a cumulative probability $U_i(t)$ that the impulse response detected at the time t has existed in voxel i, from $U_i(t',t)$; and an eighth step of calculating a time-resolved path length li in voxel i from $U_i(t)$ and s(t).

6 Claims, 5 Drawing Sheets

OTHER PUBLICATIONS

S. Arridge et al., "Optical Imaging in Medicine: II. Modeling and Reconstruction," *Phys. Med Biol.*, vol. 42, 1997, pp. 841–853.

S.B. Colak et al., "Tomographic Image Reconstruction from Optical Projections in Light–Diffusing Media," *Applied Optics*, vol. 36, No. 1, Jan. 1997, pp. 180–213.

Y. Tsuchiya et al., "Photon Migration Model for Turbid Biological Medium Having Various Shapes," *JPN. J. Appl. Phys.*, vol. 34, 1995, Part 2, pp. L79–81.

Y. Tsuchiya et al., "Frequency Domain Analysis of Photon Migration Based on the Microscopic Beer–Lambert Law," *Jpn. J. Appl. Phys.*, vol. 35, No. 9A, Sep. 1996, Part 1, pp. 4848–4851.

Y. Tsuchiya et al., "Non–invasive Spectroscopy of Variously Shaped Turbid Media Like Human Tissue Based on the Microscopic Beer–Lambert Law," *OSA Tops on Biomedical Optical Spectroscopy and Diagnostics*, vol. 3, 1996, pp. 98–100.

Y. Tsuchiya et al., "Quantitation of Absorbing Substances in Turbid Media Such as Human Tissues Based on the Microscopic Beer–Lambert Law," *Optics Communications*, vol. 144, Dec. 15, 1997, pp. 269–280.

Y. Tsuchiya et al., "Optical Quantitation of Absorbers in Variously Shaped Turbid Media Based on the Microscopic Beer–Lambert Law," *Optical Biopsy and Optical Mammography* (Annals of the New York Academy of Sciences), vol. 838, 1998, pp. 75–94.

Y. Ueda et al., "Average Value Method: A New Approach to Practical Optical Computed Tomography for a Turbid Medium Such as Human Tissue," *Jpn. J. Appl. Phys.*, vol. 37, 1998, Part 1, 5A, pp. 2717–2723.

Y.Tsuchiya, "Reconstruction of Optical CT Image Based on Microscopic Beer–Lambert Law and Average Value Method," *O Plus E*, vol. 21, No. 7, pp. 814–821.

H. Zhang et al., "Quantitation of Absorbers in Turbid Media Using Time–Integrated Spectroscopy Based on Microscopic Beer–Lambert Law," *Jpn. J. Appl. Phys.*, vol. 37, 1998, pp. 2724–2727.

H. Zhang et al., "Time Integrated Spectroscopy of Turbid Media Based on the Microscopic Beer–Lambert Law: Consideration of the Wavelength Dependence of Scattering Properties," *Optics Communications*, vol. 153, 1998, pp. 314–322.

Y. Tsuchiya et al., "Time Integrated Spectroscopy of Turbid Media Such as Human Tissues Based on the Microscopic Beer–Lambert Law," *Proceedings of JICAST'98/CPST'98, Joint International Conference on Advanced Science and Technology*, Shizuoka University, Hamamatsu, Aug. 29–30, 1998, pp. 237–240.

Y.Tsuchiya et al., "Time Integrated Spectroscopy of Turbid Media Based on the Microscopic Beer–Lambert Law: Application to Small–Size Phantoms Having Different Boundary Conditions," *Journal of Biomedical Optics*, vol. 4, Jan. 1999, pp. 183–190.

Y. Tsuchiya et al., "Analytic Expressions for Determining the Concentrations of Absorber in Turbid Media by Time-Gating Measurements," *OSA Tops, Advances in Optical Imaging and Photon Migration*, vol. 21, 1998, pp. 67–72.

H. Zhang et al., "Simple Subtraction Method for Determining the Mean Path Length Traveled by Photons in Turbid Media," *Jpn. J. Appl. Phys.*, vol. 37, Part 1, 1998, pp. 700–704.

S. Arridge, "The Forward and Inverse Problems in Time Resolved Infra–Red Imaging," *Medical Optical Tomography: Functional Imaging and Monitoring*, vol. IS11, 1993, pp. 35–64.

R. L. Barbour et al., "A Perturbation Approach for Optical Diffusion Tomography Using Continuous–Wave and Time–Resolved Data," *Medical Optical Tomography: Functional Imaging and Monitoring*, vol. IS11, 1993, pp. 87–120.

H.L., Garber et al., "A Perturbation Model for Imaging in Dense Scattering Media: Derivation and Evaluation of Imaging Operators," *Medical Optical Tomography: Functional Imaging and Monitoring*, vol. IS11, 1993, pp. 121–143.

J.C. Schotland et al., "Photon Hitting Density," *Applied Optics*, vol. 32, No. 4, Feb. 1993, pp. 448–453.

J. Chang et al., "Imaging Diffusive Media Using Time–Independent and Time–Harmonic Sources: Dependence of Image Quality on Imaging Algorithms, Target vol., Weight Matrix, and View Angles," *SPIE*, vol. 2389, 1995, pp. 448–464.

B.W. Poguel et al., "Initial Assessment of a Simple System for Frequency Domain Diffuse Optical Tomography," *Phys.Med. Biol.*, vol. 40, 1995, pp. 1709–1729.

S. Arridge, "Photon–measurement Density Functions: Part 1: Analytical Forms," Applied Optics, vol. 34, No. 31, Nov. 1, 1995, pp. 7395–7409.

* cited by examiner

METHOD OF CALCULATING OPTICAL PATH DISTRIBUTION INSIDE SCATTERING ABSORBER

TECHNICAL FIELD

The present invention relates to methods of calculating a distribution of photon paths inside a scattering medium. More particularly, the invention relates to methods of calculating a time-resolved photon path distribution inside a scattering medium, which can be applied to apparatus configured to move a light injection position and a light detection position along a surface of a measured object and gain information about the interior of the measured object.

From this time-resolved photon path distribution, we can calculate a distribution of photon paths in an appropriate measuring method and calculate contributions of respective portions of the scattering medium to an amount of optical attenuation or to a mean path length (also referred to as a contribution function or weight function).

BACKGROUND ART

In the field of optical CT or the like in a broad sense, including interior measurement, there are conventionally known measuring methods of gaining information about the interior of the measured object, using the weight function or contribution function, and a number of reports have already been made about the weight functions and others applied thereto. These are described, for example, in the following documents.

(1) S. Arridge: SPIE Institutes for Advanced Optical Technologies, Vol. IS11, Medical Optical Tomography: Functional Imaging and Monitoring, 35–64(1993); (2) R. L. Barbour and H. L. Graber: ibid. 87–120(1993); (3) H. L. Graber, J. Chang, R. Aronson and R. L. Barbour: ibid. 121–143(1993); (4) J. C. Schotland, J. C. Haselgrove and J. S. Leigh: Applied Optics, 32, 448–5453(1993); (5) Chang, R. Aronson, H. L. Graber and R. L. Barbour: Proc. SPIE, 2389, 448–464(1995); (6) B. W. Pogue, M. S. Patterson, H. Jiang and K. D. Paulsen: Phys. Med. Biol. 40, 1709–1729 (1995); (7) S. R. Arridge: Applied Optics, 34, 7395–7409 (1995); (8) H. L. Graber, J. Chang, and R. L. Barbour: Proc. SPIE, 2570, 219–234(1995); (9) A. Maki and H. Koizumi: OSA TOPS, Vol. 2, 299–304(1996); (10) H. Jiang, K. D. Paulsen and Ulf L. Osterberg: J. Opt. Soc. Am. A13, 253–266(1996); (11) S. R. Arridge and J. C. Hebden: Phys. Med. Biol. 42, 841–853(1997); (12) S. B. Colak, D. G. Papaioannou, G. W. 't Hooft, M. B. van der Mark, H. Schomberg, J. C. J. Paasschens, J. B. M. Melissen and N. A. A. J. van Astten: Applied Optics, 36, 180–213(1997).

However, the interior information measuring methods of optical CTs and others disclosed in the above documents (1) to (12) and the weight functions applied thereto included the problems discussed below and thus posed significant problems in measurement accuracy and applicability. In fact, no report has been made yet about an example of practical use of optical CT with satisfactory performance in the foregoing field.

Specifically, the first problem in the conventional optical CT and others is that the photon migration analysis or photon migration model in the medium is based on the photon diffusion equation as application of diffusion approximation to the transport equation. In other words, since the diffusion approximation holds only in media sufficiently larger than the mean free pathlength of photons in the medium, there is a problem that it is impossible to handle relatively small media, tissue of complicated interior shape, and media of complicated shape. In addition, the diffusion approximation is premised on isotropic scattering, and thus application thereof to the measurement of the measured object like living tissue having anisotropic scattering characteristics will pose a problem that there occur considerable errors due to the approximation of anisotropic scattering to isotropic scattering.

Further, differential equations such as the diffusion equation and the like involve a bothersome problem that even with any numerical computation approach such as the analytical or finite element method, boundary conditions (the shape of the medium, reflection characteristics at interfaces, etc.) must be preliminarily set and then a solution can be determined. Namely, in the case of the measured object like living tissue, the boundary conditions normally vary depending upon a place to be measured, the wavelength of light used in measurement, and so on, and for improvement in accuracy on the basis of correction for influence of these factors, it is necessary to repeat complicated calculations at every change of the boundary conditions, which results in a big problem of extremely long calculation time.

The second problem is that the weight function in a narrow sense (also called the contribution function), i.e., a mean path length (weighted mean) for an ensemble of photons constituting an impulse response of the medium, or a phase delay equivalent thereto (measured in the frequency domain) is applied to the calculation of the information on the interior of the measured object. In this case, the weight function in a narrow sense (the mean path length or the phase delay equivalent thereto) varies depending upon absorption coefficients and absorption distribution, and thus handling thereof is extremely complicated. Since practical use of a calculation method taking account of such dependence inevitably requires calculations in a large iteration number, there will arise a problem that the calculation time becomes extremely long over a practical range. Therefore, the dependence on the absorption coefficients and absorption distribution is normally ignored, but this approximation can be the cause of a serious issue of increase in errors.

In order to reduce the errors due to the dependence of the weight function on the absorption coefficients and absorption distribution as described above, there is a method of calculating and applying the weight function with some appropriate absorption. However, this poses a problem that the time necessary for the calculation of the weight function with absorption is extremely longer than the time necessary for the calculation of the weight function without absorption.

For the reason described above, it is concluded that the conventional measuring methods using the weight function in a narrow sense (the mean path length or the phase delay equivalent thereto) are not practical.

Besides the application of the above weight function in a narrow sense, there is a further measuring method of applying the perturbation theory to the approximate equation of the transport equation or to the photon diffusion equation to gain the information about the interior of the measured object with the use of the relationship between signal light and optical characteristics of the scattering medium. However, this method requires extremely complex handling of the nonlinear effects (second and higher order terms). In this respect, the calculation including the second and higher order terms can be theoretically performed by a computer, but the calculation time will be huge even with the use of the currently fastest computer, so as to make practical use thereof impossible. It is thus common practice to ignore the second and higher order terms. For this reason, this method had a problem that there arose large errors due to interaction between absorbing regions in reconstruction of an optical CT image of a medium containing a plurality of relatively strong absorbing regions.

As described above, the measuring methods of gaining the information about the interior of the measured object, such as the conventional optical CT and the like, failed to obtain a reconstructed image with satisfactory accuracy and had the significant issues as to the spatial resolution, image distortion, quantitation, measurement sensitivity, required measurement time, and so on, which made practical use thereof difficult.

The Inventor contemplated that the following was important in order to break through the above circumstances, and has pursued a series of studies. Namely, an important subject for achievement of a measuring method capable of obtaining the information about the interior of the measured object, particularly, for achievement of optical CT, is to clarify the details of behavior of photons migrating in living tissue as a strong scattering medium, more precisely describe the relation between detected signal light and the optical characteristics of the scattering medium (scattering absorber) containing an absorptive constituent, and develop a new algorithm of reconstructing an optical CT image by making use of the signal light and the relation between the signal light and the optical characteristics of the scattering medium. Then the Inventor contemplated applying the Microscopic Beer-Lambert Law (hereinafter referred to as "MBL") to the analysis of the behavior of photons migrating in the scattering medium and making use of information about the photon path distribution, i.e., about where photons have passed, for the reconstruction of optical CT image.

Then the Inventor has proposed a photon migration model (a finite grid model) corresponding to the scattering media, based on the MBL, derived an analytic equation representing the relation between the optical characteristics of the scattering media and the signal light, and developed methods of analyzing the behavior of photons in the scattering media. The Inventor and others reported the results of these, for example, in the following documents.

(13) Y. Tsuchiya and T. Urakami: "Photon migration model for turbid biological medium having various shapes", Jpn. J. Appl. Phys. 34. Part 2, pp. L79–81(1995); (14) Y. Tsuchiya and T. Urakami, "Frequency domain analysis of photon migration based on the microscopic Beer-Lambert law", Jpn. J. Appl. Phys. 35, Part 1, pp. 4848–4851(1996); (15) Y. Tsuchiya and T. Urakami: "Non-invasive spectroscopy of variously shaped turbid media like human tissue based on the microscopic Beer-Lambert law", OSA TOPS, Biomedical Optical Spectroscopy and Diagnostics 1996, 3, pp. 98–100(1996); (16) Y. Tsuchiya and T. Urakami: "Quantitation of absorbing substances in turbid media such as human tissues based on the microscopic Beer-Lambert law". Optics Commun. 144, pp. 269–280(1997); (17) Y. Tsuchiya and T. Urakami: "Optical quantitation of absorbers in variously shaped turbid media based on the microscopic Beer-Lambert law: A new approach to optical computerized tomography", Advances in Optical Biopsy and Optical Mammography (Annals of the New York Academy of Sciences), 838, pp. 75–94(1998); (18) Y. Ueda, K. Ohta, M. Oda, M. Miwa, Y. Yamashita, and Y. Tsuchiya: "Average value method: A new approach to practical optical computed tomography for a turbid medium such as human tissue", Jpn. J. Appl. Phys. 37, Part 1. 5A, pp. 2717–2723(1998); (19) Yutaka Tsuchiya; "Reconstruction of optical CT image based on Microscopic Beer-Lambert Law and average value method," O plus E, Vol. 21, No.7, 814–821; (20) H. Zhang, M. Miwa, Y. Yamashita, and Y. Tsuchiya: "Quantitation of absorbers in turbid media using time-integrated spectroscopy based on microscopic Beer-Lambert law", Jpn. J. Appl. Phys. 37, Part 1, pp. 2724–2727(1998); (21) H. Zhang, Y. Tsuchiya, T. Urakami, M. Miwa, and Y. Yamashita: "Time integrated spectroscopy of turbid media based on the microscopic Beer-Lambert law: Consideration of the wavelength dependence of scattering properties", Optics Commun. 153, pp. 314–322(1998); (22) Y. Tsuchiya, H. Zhang, T. Urakami, M. Miwa, and Y. Yamashita: "Time integrated spectroscopy of turbid media such as human tissues based on the microscopic Beer-Lambert law", Proc. JICAST'98/CPST'98, Joint international conference on Advanced science and technology, Hamamatsu, August 29–30, pp. 237–240(1998); (23) H. Zhang, T. Urakami, Y. Tsuchiya, Z. Liu, and T. Hiruma: "Time integrated spectroscopy of turbid media based on the microscopic Beer-Lambert law: Application to small-size phantoms having different boundary conditions", J. Biomedical Optics. 4, pp. 183–190(1999); (24) Y. Tsuchiya, Y. Ueda, H. Zhang, Y. Yamashita, M. Oda, and T. Urakami: "Analytic expressions for determining the concentrations of absorber in turbid media by time-gating measurements", OSA TOPS, Advances in Optical Imaging and Photon Migration, 21, pp. 67–72(1998); (25) H. Zhang, M. Miwa, T. Urakami, Y. Yamashita, and Y. Tsuchiya: "Simple subtraction method for determining the mean path length traveled by photons in turbid media", Jpn. J. Appl. Phys. 37, Part 1, pp. 700–704 (1998).

This MBL is the law that "in a microscopic view in a medium having arbitrary scattering and absorption distributions, a photon migrating in a portion having the absorption coefficient of $\mu_a$, is exponentially attenuated because of absorption along a migrating zigzag photon path of length l, a survival probability of the photon is given by the value $\exp(-\mu_a l)$ independent of the scattering characteristics of the medium and the boundary conditions, and the amount of attenuation due to the absorption is $\mu_a l$," and is expressed, for example, by the following equation.

$$f(l) = f^0(l)\exp(-\mu_a l) \tag{1}$$

Here f(l) is a detection probability density function of photons actually measured, and $f^0(l)$ a detection probability density function of photons in a state of no absorption.

This Eq (1) indicates that in the medium having arbitrary scattering and absorption distributions, absorption and scattering events are independent of each other and that the superposition principle holds as to the absorption, i.e., that, in the case of the medium with the scattering and absorption distributions being a multiple component system, the total absorbance is given by the sum of absorbances of respective components.

The Inventor and others derived equations expressing the relations between various optical responses and optical characteristics of scattering media from the MBL represented by above Eq (1) and clarified that it was possible to describe the various responses of scattering media by an attenuation term dependent upon absorption and a term independent of absorption, separated from each other. This made it feasible to quantify the absolute value of the concentration of the absorptive constituent in the scattering medium from the relation between the absorption coefficient and the extinction coefficient specific to the absorptive constituent, based on spectral measurement of the attenuation term through use of light of multiple wavelengths.

The measuring methods based on the MBL as described above have the major feature of being theoretically unsusceptible to the shape of the medium, the boundary conditions, and the scattering, and are applicable to anisotropic scattering media and small media. However, the absorption coefficient and the absorber concentration measured herein can be correctly measured for scattering media with uniform absorption, but measurement for heterogeneous media with nonuniform absorption distribution provides a mean absorption coefficient and a mean concentration (weighted mean for photon path distribution) of photon-passing portions. Accordingly, there arose the need for determining the photon path distribution, in order to realize high-accuracy optical CT.

Then the Inventor and others further expanded the methods of analyzing the behavior of photons in the scattering media on the basis of the MBL and have developed various measuring methods applicable even to the heterogeneous scattering media (heterogeneous system) with nonuniform distributions of scattering and absorption and capable of quantitatively measuring a concentration distribution of an absorptive constituent in a scattering medium without being affected by the shape of the medium, the scattering characteristics, and so on.

Specific measuring methods derived based on the MBL heretofore by the Inventor and others include, for example, the time-resolved spectroscopy (TRS) making use of the impulse response, the time-integrated spectroscopy (TIS) making use of the time integral of the impulse response, the time-resolved gating integral spectroscopy (TGS) making use of the time-gating integral of the impulse response, the phase modulation spectroscopy (PMS) in the frequency domain, the reconstruction method of optical CT image based on the average value method (AVM), and so on. These measuring methods are described in Japanese Patent Application No. 10-144300, aforementioned Document (7), and aforementioned Documents (15) to (25).

The materialization of the new measuring methods as described above drastically improved the measurement accuracy, but the reconstruction methods of optical CT image still used the conventional weight function, i.e., the mean path length or the phase delay equivalent thereto. Specifically, a small change is given to an absorption coefficient of voxel i in an imaginary medium with a uniform absorption coefficient $\mu_{84}$ described by the finite grid model, its optical output is calculated by making use of the Monte Carlo calculation, the numerical calculation of the Path Integral and the transport equation, the numerical calculation of the photon diffusion equation, or the like, and the weight function (or the contribution function) Wi of voxel i is determined corresponding to the difference between optical outputs before and after the change, i.e., the deviation of light intensity, optical path length, attenuation, or the like with respect to the imaginary medium having the uniform absorption coefficient $\mu_v$.

DISCLOSURE OF THE INVENTION

However, the above-stated conventional measuring methods of determining the weight function (or the contribution function) corresponding to the various measuring methods by changing the absorption coefficient of voxel i in the imaginary medium described by the finite grid model, required that the forward problem calculation such as the photon diffusion equation or the like should be executed the number of times equal to the total number of voxels, and thus had the problem of extremely long calculation time and, in turn, the problem of very long measurement time. In this case, there was also the problem of insufficient measurement accuracy in the measuring methods using the conventional weight function in a narrow sense (the mean path length or the phase delay equivalent thereto). For improvement in the measurement accuracy, the calculation time became much longer, so as to result in the problem of longer measurement time.

The present invention has been accomplished in view of the conventional problems as described above, and an object of the invention is to provide a method that permits precise and quick calculation of a distribution of photon paths inside a scattering absorber of a heterogeneous system like living tissue. The photon path distribution calculated in this way permits us to quickly calculate the weight function Wi corresponding to each of the various specific measuring methods for quantitatively measuring the concentration distribution of the absorptive constituent inside the scattering medium.

In order to achieve the above object, the Inventor has conducted elaborate research on analytic methods and others based on the MBL, and found that a time-resolved path length li in voxel i of a measured medium divided into N ($1 \leq N$) voxels was equal to a time-resolved path length li in voxel i (i=1, 2, . . . , N; $1 \leq N$) of an imaginary medium assumed to have the same scattering characteristics and boundary conditions as the measured medium but absorb no light, that this time-resolved path length li in voxel i of the imaginary medium could be described by a photon existence probability or the like in voxel i (i=1, 2, . . . , N; $1 \leq N$) of the imaginary medium, and that the time-resolved path length li in voxel i of this imaginary medium could be directly and quickly calculated by making use of the result of calculation of photon migration in the imaginary medium by the Monte Carlo calculation, the numerical calculation of the path integral, the transport equation, or the photon diffusion equation, or the like, thereby accomplishing the present invention.

The conventional Monte Carlo calculation is based on the fundamental theory of counting the number of occurrences of scattering events in voxel i in the finite grid model, and this concept is also followed and is applied to the conventional weight function. On this occasion, if the scattering characteristics in voxel i are uniform, the path length can be estimated from the relation between the number of scattering events and the mean free pathlength. However, if the scattering characteristics are nonuniform in voxel i, the relation between the number of scattering events and the mean free pathlength is dependent upon a scattering distribution and becomes complicated, and it is thus infeasible to accurately determine the time-resolved path length being the objective of the present invention. Accordingly, in order to circumvent the conventional problem as described, the present invention employs a new technique of calculating the time-resolved path length li in voxel i from the photon existence probability or the like in voxel i of the medium.

Specifically, a method of calculating a distribution of photon paths inside a scattering medium according to the present invention is a method comprising:

a first step of dividing a measured medium being the scattering medium, into N ($1 \leq N$) voxels each having a predetermined size and assumed to have a uniform absorption distribution in a measurement wavelength region;

a second step of hypothesizing an imaginary medium that can be assumed to have the same shape, boundary conditions, and scattering distribution as the measured medium, have a uniform refractive index distribution, and be nonabsorbing, for the measured medium divided into the N voxels;

a third step of setting a light injection position for injection of impulse light, and a light detection position for detection of an impulse response s(t) at a time t of the impulse light having been injected at the light injection position and having propagated in the imaginary medium, on a surface of the imaginary medium;

a fourth step of calculating the impulse response s(t) detected at the light detection position after injection of the impulse light at the light injection position into the imaginary medium;

a fifth step of calculating a photon existence probability density $U_i(t',t)$ that an ensemble of photons constituting the impulse response s(t) detected at the time t at the light detection position after injection of the impulse light at the light injection position into the imaginary medium has existed in an arbitrary voxel i (i=1, 2, ..., N; 1≦N) in the imaginary medium at a time t' (0≦t'≦t) before the detection at the light detection position;

a sixth step of calculating a photon existence cumulative probability $U_i(t)$ that the ensemble of photons constituting the impulse response s(t) detected at the time t at the light detection position has existed in said voxel i, using the photon existence probability density $U_i(t',t)$; and a seventh step of calculating a time-resolved path length li in the voxel I, using the photon existence cumulative probability $U_i(t)$ and the impulse response s(t).

Conventionally, a small change was given to the absorption coefficient in voxel i of the imaginary medium described by the finite grid model and the various weight functions Wi were calculated from a calculated value of a ratio of intensities of output light before and after the change of the absorption coefficient, a difference between attenuation amounts, or the like. This method required that the forward problem calculation of the photon diffusion equation or the like should be executed the number of times equal to the total number N of voxels, and thus required the long calculation time, so as to result in the serious problem of very long measurement time, whereas the above method solved this problem. Moreover, since the time-resolved path length li is calculated for the nonabsorbing medium in the above method, it also solved the problem that a long time was consumed for the forward problem calculation of the photon diffusion equation or the like for the absorbing medium in the conventional methods.

In the method of the present invention, parameters of all the voxels are calculated in parallel for the set consisting of a pair of the light injection position and detection position, so that the calculation time can be reduced more. Namely, the method of calculating the distribution of photon paths inside the scattering medium according to the present invention is the method first having permitted direct, precise, and quick calculation of the time-resolved path length li.

For specifically determining the time-resolved path length li in voxel i, as described hereinafter, thought is given to the photon existence probability density $U_i(t',t)$ that the ensemble of photons with the path length of l constituting the impulse response s(t) detected at the time t at the light detection position after injection of the impulse light at the light injection position into the finite grid model, has existed in the voxel i at the time t' (0≦t'≦t) before the detection at the light detection position.

The photon existence probability density $U_i(t',t)$ in the voxel i at the time t', which is described by introducing the new time variable t', can be expressed as follows by applying the reciprocity theorem.

$$U_i(t',t) = U_{pi}(t')U_{qi}(t-t') \quad (2.2)$$

[In the above equation, $U_{pi}(t')$ indicates a photon existence probability density that photons injected at the light injection position p at the time t'=0 exist in the voxel i at the time t'=t', and $U_{qi}(t-t')$ indicates a photon existence probability density that photons injected at the light detection position q at the time t-t'=0 exist in the voxel i at the time t-t'.]

The above $U_i(t',t)$ can be determined by calculating two forward problems as indicated by Eq (2.2). At this time, $U_{pi}(t')$ can be calculated by injection of the impulse light at the light injection position p of the finite grid model. $U_{qi}(t-t')$ can also be calculated by injection of the impulse light at the light detection position q of the finite grid model. A specific method of calculating the two forward problems represented by Eq (2.2) will be detailed later.

Since the present invention permits quick and direct calculation of the time-resolved path length li in the voxel i, it is further feasible to quickly calculate the weighted mean Li of the time-resolved path length li with respect to time, using it.

Since there was no specific calculation method of the time-resolved path length li known heretofore, no idea was proposed about such an approach that the time-resolved path length li was first determined and then the weighted mean Li of the time-resolved path length li and the weight function Wi were calculated based thereon. Actually, no report has been made heretofore on an example of the measuring method of direct calculation and utilization of the time-resolved path length li.

Since the present invention permits the quick and direct calculation of the time-resolved path length li in the voxel i, it is further feasible to quickly calculate the weight functions Wi corresponding to a variety of predetermined specific measuring methods for quantitatively measuring the concentration distribution of the absorptive constituent inside the measured medium, using it.

Namely, the Inventor and others have already clarified the relations of the time-resolved path length li in the voxel i in the measured medium with measured values by the various measuring methods and the corresponding weight functions in the specific measuring methods of TRS, TIS, TGS, PMS, AVM, etc. based on the MBL, in the case of use of the measured medium and the finite grid model resulting from the division of the corresponding imaginary medium into N voxels.

For example, the weight function for the attenuation amount is equivalent to the time-resolved path length li itself in TRS, and in TIS it is described using the weighted mean Li (also referred to as the mean path length Li) of the time-resolved path length li with respect to time, the variance of the time-resolved path length li, or the like. More specifically, the TIS and AVM making use of the attenuation amount and the mean path length employ the weight functions Wi described using the relations of the time-resolved path length li in the voxel i in the measured medium with the mean path length Li being the weighted mean, the variance of the time-resolved path length li, etc., and it is known that these can be expressed by Eqs (7), (9), and (12) as described hereinafter.

Here "time-resolved photon path distribution" in the method of calculating the photon path distribution inside the scattering medium according to the present invention refers, as shown in FIG. 1, to a photon path distribution of an ensemble of photons with the path length of l constituting an impulse response B measured at the light detection position q on the finite grid model 10 in the case where the three-dimensional measured medium is assumed as the finite grid model 10 divided into N (1≦N) voxels 20 (volume elements) and where impulse light A is injected at the light injection position p on the finite grid model 10. Specifically, this time-resolved photon path distribution is represented by an N-dimensional vector [li] having elements of time-resolved path lengths li of the voxels i (i=1, 2, ..., N; 1≦N). From the above definition, this time-resolved photon path distribution is a function of path length l, i.e., a function of time t. The attenuation amount of output light signal in the various specific measuring methods is expressed by a function of the product of the time-resolved path length li and the absorption coefficient of the voxel i. The weighted mean Li of the time-resolved path length li for time is called a mean path length in voxel i, and an N-dimensional vector [Li] having elements thereof of weighted means is called a mean path length distribution. In the present specification, each "voxel 20" in FIG. 1 and FIG. 2 will be denoted by "voxel i" instead of "voxel 20" for convenience' sake of description.

Further, the weight function is defined as a contribution of absorption information to a physical quantity of interest. For example, the weight function for the time-resolved attenuation amount obtained in TRS is independent of absorption and absorption distribution, there is the relation: [time-resolved attenuation amount]=[weight function]·[absorption coefficient difference], and this weight function is equivalent to the time-resolved path length li obtained above. The weight function for the attenuation amount obtained by the time integral of the impulse response (TRS) is defined by [TRS attenuation amount]=[weight function]·[absorption coefficient difference], and the weight function for the mean path length difference is defined by [mean path length difference]=[weight function]·[absorption coefficient difference]. In the case of TRS, these weight functions are functions of absorption coefficient.

By introducing these weight functions, the matrix equation for reconstruction of image in optical CT can be described as the product of matrices, i.e., as [weight function]·[absorption coefficient difference], and the [absorption coefficient difference] or absorption distribution can be calculated from this equation.

The scattering characteristics of the foregoing measured medium and imaginary medium can be heterogeneous, and the specific calculation of the forward problems can be performed utilizing the Monte Carlo calculation, the numerical calculation of the Path Integral or the transport equation, the numerical calculation of the photon diffusion equation, and so on.

There are no specific restrictions on the "predetermined measuring methods" to which the time-resolved path length li determined by the method of calculating the photon path distribution inside the scattering medium according to the present invention is applied, and the predetermined measuring methods can be, for example, the interior measuring methods for the scattering medium such as the time-resolved spectroscopy (TRS), the time integral spectroscopy (TIS), the time-resolved gating integral spectroscopy (TGS), the phase modulation spectroscopy in the frequency domain (PMS), the reconstruction method of optical CT image based on the average value method (AVM), and so on derived based on the MBL by the Inventor and others, and can also be the measuring methods with no base on the MBL, as described in foregoing Documents (1) to (12).

Another method of calculating a distribution of photon paths inside a scattering medium according to the present invention is a method comprising:

a first step of dividing a measured medium being the scattering medium, into N (1≦N) voxels each having a predetermined size and assumed to have a uniform absorption distribution in a measurement wavelength region;

a second step of hypothesizing an imaginary medium that can be assumed to have the same shape, boundary conditions, and scattering distribution as the measured medium, have a uniform refractive index distribution, and be nonabsorbing, for the measured medium divided into the N voxels;

a third step of setting a light injection position for injection of impulse light, and a light detection position for detection of an impulse response s(t) at a time t of the impulse light having been injected at the light injection position and having propagated in the imaginary medium, on a surface of the imaginary medium;

a fourth step of calculating a photon existence probability density $U_i(t',t)$ that an ensemble of photons constituting the impulse response s(t) detected at the time t at the light detection position after injection of the impulse light at the light injection position into the imaginary medium has existed in an arbitrary voxel i (i=1, 2, ..., N; 1≦N) in the imaginary medium at a time t' (0≦t'≦t) before the detection at the light detection position;

a fifth step of calculating a photon existence cumulative probability $U_i(t)$ that the ensemble of photons constituting the impulse response s(t) detected at the time t at the light detection position has existed in said voxel i, using the photon existence probability density $U_i(t',t)$;

a sixth step of calculating a sum U(t) of said photon existence cumulative probabilities $U_i(t)$ for all the voxels; and a seventh step of calculating a time-resolved path length li in the voxel i, using the photon existence cumulative probability $U_i(t)$ and the sum U(t) of the photon existence cumulative probabilities $U_i(t)$ for all the voxels.

In the above case, the time-resolved path length li in the voxel i can be quickly and directly calculated, and thus the weighted mean Li of the time-resolved path length li with respect to time can be quickly calculated using it. Since the time-resolved path length li in the voxel i can be quickly and directly calculated, it is feasible to quickly calculate the weight functions Wi corresponding to the various predetermined specific measuring methods for quantitatively measuring the concentration distribution of the absorptive constituent inside the measured medium, using it.

BEST MODE FOR CARRYING OUT THE INVENTION

Figure 1:
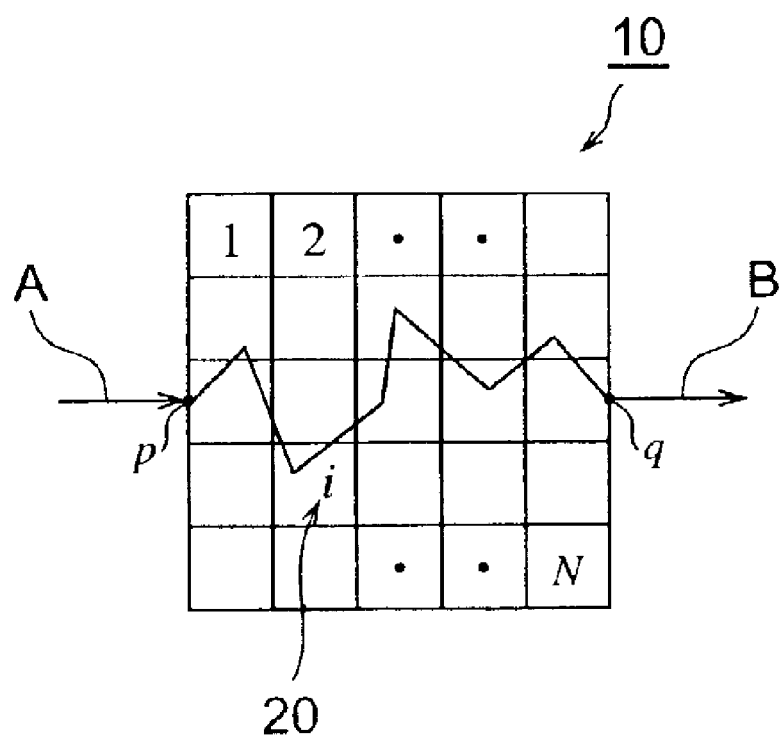
FIG. 1 is a schematic illustration showing a finite grid model for analysis of photon migration inside a measured medium.

The preferred embodiments of the method of calculating the photon path distribution inside the scattering medium according to the present invention will be described below in detail with reference to the drawings. In the following description the same or equivalent portions will be denoted by the same reference symbols and redundant description will be omitted. Although consideration using three-dimensional coordinates is necessary for photons traveling while being scattered in the scattering medium, the following description will be sometimes given using two-dimensional coordinates for simplicity of description.

The principle of the present invention will be described first.

[Principle of the Invention]

As described previously, the analytic methods of analyzing the behavior of light in the scattering medium, which have been developed based on the MBL by the Inventor and others, can be applied to the heterogeneous scattering media (heterogeneous system) with nonuniform distributions of scattering and absorption. It is then deduced from the analytic methods based on the MBL that various optical responses (light outputs) from the heterogeneous scattering media can be described by separating them into the attenuation term dependent upon absorption and the term independent of absorption and that the attenuation term of optical response can be described by the photon path distribution and absorption distribution in the measured medium. Accordingly, if the photon path distribution in the measured medium can be known in advance, it will be feasible to implement optical CT or the like of quantifying a concentration distribution of an absorptive constituent inside the measured medium. Namely, important points for implementing the optical CT are to know the photon path distribution inside the measured medium and to develop a method of quickly calculating the photon path distribution.

The present invention is based on such starting points that the items (i) to (v) below hold in the measured medium and in the finite grid model of the corresponding imaginary medium.

Specifically, (i) supposing the refractive index distribution inside the measured medium is uniform, the relation of $l=ct$ always holds for the impulse response (time-resolved waveform) of the measured medium, where $l$ is the path length, $c$ the speed of photons in the measured medium determined by the refractive index, and $t$ the time. The reason why the refractive index distribution in the measured medium is supposed to be uniform herein is that, where the heterogeneous scattering medium like living tissue is selected as a measured medium, the major ingredient of the living tissue is water and the refractive index distribution thereof can be assumed uniform. Therefore, the following description will concern the measured medium with a uniform refractive index distribution unless otherwise stated.

(ii) Since scattering and absorption are independent of each other, the photon path distribution of an ensemble of photons (detected as an impulse response) constituting an impulse response, i.e., the time-resolved photon path distribution is uniquely determined once the light injection position and light detection position are set for a heterogeneous medium with arbitrary distributions of scattering and absorption.

(iii) The aforementioned photon path distribution is given by a function of time, is independent of the number of injected photons (i.e., photon density) and of the absorption and absorption distribution of the measured medium, and is equivalent to a photon path distribution on the assumption that there occurs no absorption in the measured medium. When a three-dimensional measured medium is divided into N ($1 \leq N$) voxels (volume elements) each having a predetermined size, the photon path distribution of the ensemble of photons having the path length of $l$ can be expressed by an N-dimensional vector [li] having elements of path lengths li in the respective voxels i (i=1, 2, . . . , N; $1 \leq N$).

(iv) This time-resolved photon path distribution [li] can be calculated by assuming an imaginary medium having the same scattering characteristics (which can be heterogeneous) and boundary conditions as the measured medium, having uniform refractive index distribution, and being nonabsorbing.

(v) The various weight functions Wi used for a variety of optical CT image reconstruction algorithms can be described using the time-resolved path length li in each voxel i defined above.

The Inventor proposed the optical CT for measuring the concentration distribution of the absorptive constituent in the heterogeneous medium, using the weight function Wi described using the time-resolved photon path distribution li and actually measured values for the measured medium (Japanese Patent Application No. 10-144300 and Document (19)).

FIG. 1 shows the finite grid model for analysis of photon migration inside a heterogeneous scattering absorber as a measured medium.

Further, the finite grid model 10 shown in FIG. 1 also indicates an imaginary medium (which will be denoted by the same reference symbol as the measured medium) assumed to have the same shape, scattering distribution, and boundary conditions as the measured medium, have a uniform refractive index distribution, and be nonabsorbing, as well as the measured medium. In this case, the three-dimensional measured medium is divided into N ($1 \leq N$) voxels (volume elements) and the voxels are denoted by respective numbers i (i=1, 2, . . . , N; $1 \leq N$). Therefore, the imaginary medium assumed corresponding to the measured medium also has N voxels similarly.

Figure 2:
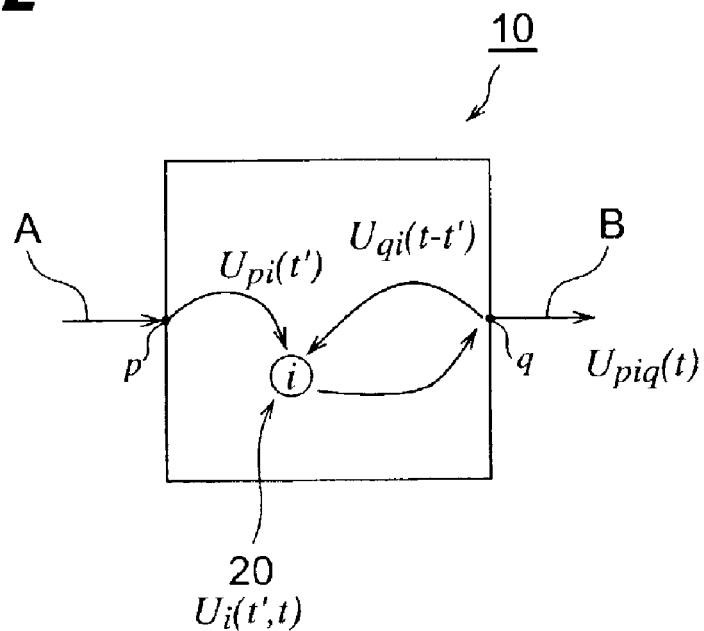
FIG. 2 is a schematic illustration showing paths of a photon ensemble having passed the voxel i and a probability thereof among an ensemble of photons (having the path length of l) constituting an impulse response B detected at the time t at the light detection position q in the case where the impulse light A is injected at the light injection position p in the finite grid model shown in FIG. 1.

It is noted herein that in the following description, when the absorption coefficient of the medium represented by the finite grid model 10 in FIGS. 1 and 2 is zero, the "impulse response B" will be sometimes described by designating it as "impulse response s(t)," i.e., a response without absorption. When the absorption coefficient of the medium represented by the finite grid model 10 is not zero on the other hand, the "impulse response B" will be sometimes described by designating it as "impulse response h(t)," i.e., a response with absorption.

The size and shape of the voxel i in the finite grid model 10 of the imaginary medium shown in FIG. 1 are determined within the range and shape in which an absorption distribution in the voxel i of the corresponding measured medium is assumed uniform or can be safely assumed uniform. This is because the absorption distribution data in each voxel i obtained by actual measurement is obtained as an average of absorption distributions in each voxel i. Once the size and the shape of voxel i are determined, the total number of all voxels is also determined. Namely, the size and shape of each voxel i and the total number of all voxels of the imaginary medium can be arbitrarily determined as long as the absorption can be assumed uniform in the voxel i, as described previously. The practical size and shape of voxel i are determined according to the measuring methods used, or according to the resolutions of CT image required by those measuring methods.

In the method of calculating the photon path distribution inside the scattering medium according to the present invention, in the case where the impulse light A is injected at the light injection position p on the finite grid model 10 of the imaginary medium shown in FIG. 1, an ensemble of photons having the path length of l is considered among the impulse response B, i.e., h(t) measured at the light detection position q of the finite grid model 10. Here the light injection position p and light detection position q are arbitrary.

In the case where the impulse light (injected impulse) A consisting of a number of photons is injected into the finite grid model 10 shown in FIG. 1, the impulse response B, or h(t) contains photons having various path lengths, but at a given observation time t the path length l is uniquely determined as l=ct. There exist a lot of photons having the path length of l. Then let us define that the photon path distribution of the ensemble of photons having the path length of l, i.e., path lengths li in the respective voxels i (i=1, 2, ..., N; 1≦N) are represented by a probability distribution of photon paths that the photons can pass. In conjunction therewith, the photon path distribution in the voxels i in the finite grid model 10 is expressed by an N-dimensional vector [li] having elements of time-resolved path lengths li in the voxels i. Since there exist a lot of photons having the path length of l, as described previously, the time-resolved path length li in each voxel i is an average (ensemble mean) of path lengths of these individual photons in the voxel i. In the system as described, once the light injection position p and the light detection position q are determined, the time-resolved photon path distribution [li] of the ensemble of photons constituting the impulse response B or h(t) is uniquely determined.

Since the time-resolved photon path distribution [li] of the ensemble of photons constituting the impulse response h(t) of the measured medium described above is independent of absorption of the measured medium, it is equivalent to the time-resolved photon path distribution [li] of the ensemble of photons constituting the impulse response s(t) of the imaginary medium assumed to be nonabsorbing. Namely, by determining the time-resolved photon path distribution [li] of the ensemble of photons constituting the impulse response s(t) of the imaginary medium, it is feasible to determine the time-resolved photon path distribution [li] of the ensemble of photons constituting the impulse response h(t) of the measured medium.

1. General Description of Analysis Model and Analysis

First described is the relation of the attenuation amount, path length, etc. in the measured medium being a heterogeneous scattering medium. Since the absorption and scattering phenomena are independent of each other, we can assume herein that the imaginary medium 10 shown in FIG. 1 has the same absorption distribution as the measured medium. However, the other conditions are the same as in the case of the finite grid model 10 of the measured medium.

Then the relation between the path length l and the path length distribution li is first given by the following equation from the aforementioned knowledges (i) to (v) and the MBL.

$$\sum_{i=1}^{N} l_i = l \tag{2}$$

[In the equation, i indicates each of numbers (i=1, 2, ..., N; 1≦N) of the N voxels in the measured medium, and li the time-resolved path length in voxel i.]

When the measured medium is a heterogeneous scattering medium, the impulse response h(t) is given by the following equation corresponding to Eq (1).

$$h(t) = s(t) \exp\left[-\sum_{i=1}^{N} (\mu_{ai} l_i)\right] \tag{3}$$

$$\frac{\partial \ln h(t)}{\partial \mu_{ai}} = -l_i \tag{4}$$

$$\ln h(t) = \ln s(t) - \sum_{i=1}^{N} \int_{0}^{\mu_{ai}} l_i d\mu_a \tag{5}$$

$$= \ln s(t) - \sum_{i=1}^{N} (\mu_{ai} l_i)$$

[In the equations, $\mu_{ai}$ indicates the absorption coefficient of the voxel i, s(t) the impulse response of the imaginary medium detected at the detection position q of the imaginary medium on the assumption of the measured medium being nonabsorbing, and h(t) the impulse response of the measured medium detected at the detection position q. The last term (on the right side) in Eq (5) is derived from the fact that the time-resolved path length li is independent of absorption and absorption distribution.]

Eq (4) and Eq (5) represent the differential form and the integral form, respectively, of the impulse response h(t) represented by Eq (3). It is seen from Eq (5) that the impulse response h(t) of the heterogeneous scattering medium can be described by separating it into the term independent of absorption, lns(t), and the attenuation term dependent upon absorption, which is represented by Eq (16) below.

$$\sum_{i=1}^{N} (\mu_{ai} l_i) \tag{16}$$

Further, it is seen from Eq (5) that the attenuation amount of the optical response, ln[h(t)/s(t)], can be described by the time-resolved photon path distribution [li] and the absorption distribution [$\mu_{ai}$] in the measured medium. Attention has to be paid herein to the fact that the time-resolved photon path distribution in the measured medium is equivalent to the time-resolved photon path distribution in the imaginary medium, i.e., in the nonabsorbing medium. In the time-resolved spectroscopy (TRS), therefore, the weight function for the attenuation amount is equal to the time-resolved path length distribution [li], and it becomes feasible to implement reconstruction of optical CT image making use of this relation. Such time-resolved optical CT is substantiated by the easiest image reconstruction algorithm.

More general optical CT includes the TIS making use of the time integral of the above impulse response h(t), the TGS making use of the integral of the impulse response h(t) in a predetermined time range, the PMS making use of sinusoidal modulated light, and the AVM of providing the imaginary medium with uniform absorption as a reference and measuring deviations from the reference, in those various methods. For all of these methods, however, we can derive the fact that the attenuation amount or the deviation of attenuation amount can be described by separating it into the attenuation term dependent upon absorption and the term independent of absorption and the fact that the attenuation amount or the attenuation amount deviation of the various optical responses can be described by the time-resolved photon path distribution and the absorption distribution in the measured medium, and determine the weight function for the attenuation amount or the attenuation amount deviation from this relation. As described hereinafter, it is also derived that the weight function for the attenuation amount or the attenuation amount deviation in the TIS and PMS can be described by the mean path length or the phase delay, and their higher-order partial differential coefficients.

For example, the optical response in the TIS is equivalent to the time integral of the aforementioned impulse response h(t) and can be expressed as in the following equation.

$$I = \int_0^\infty h(t)dt = \int_o^\infty s(t)\exp\left[-\sum_{i=1}^N (\mu_{ai} l_i)\right] dt \quad (6)$$

[In the equation, I indicates the time integral of the impulse response h(t) of the heterogeneous system.]

The differential form and integral form of Eq (6) can be expressed as in the following equations, similar to Eq (4) and Eq (5) corresponding to Eq (3).

$$\frac{\partial \ln I}{\partial \mu_{ai}} = -\frac{\int_0^\infty l_i s(t) \exp\left[-\sum_{i=1}^N (\mu_{ai} l_i)\right] dt}{\int_0^\infty s(t)\exp\left[-\sum_{i=1}^N (\mu_{ai} l_i)\right] dt} \quad (7)$$

$$= -\langle l_i \rangle = -L_i$$

$$\ln I = \int_0^\infty s(t)dt - \sum_{i=1}^N \int_0^{\mu_{ai}} L_i(\mu_a) d\mu_a \quad (8)$$

[In Eqs (7) and (8), Li indicates the mean path length Li in voxel i of an ensemble of photons constituting the time integral I detected at the detection position, i.e., the weighted mean <li> of the aforementioned time-resolved path length li.]

This mean path length (weighted mean of the time-resolved path length li) Li is dependent upon the scattering characteristics, boundary conditions, and absorption and absorption distribution of the scattering medium. On this occasion, attention has to be paid to the fact that the integral in the second term on the right side in Eq (8) cannot be expressed by the product, different from Eq (5). Accordingly, the weight function for the attenuation amount is not the simple mean path length Li, but is dependent upon absorption, which makes optical CT reconstruction algorithms complex.

In the AVM measurement of providing the imaginary medium with uniform absorption as a reference and measuring the measured medium as deviations from the reference, the attenuation amount difference (attenuation amount deviation) ΔBi between the measured medium and the imaginary medium in voxel i is expressed as in the equation below, using the absorption coefficient difference (absorption coefficient deviation) $\Delta\mu_{ai}$ and the weight function Wi.

$$\Delta B_i(\mu_{ai}) = \Delta\mu_{ai} W_i \quad (9)$$

$$\Delta\mu_{ai} = \mu_{ai} - \mu_v \quad (10)$$

$$\Delta B_i(\mu_{ai}) = B_i(\mu_{ai}) - B_i(\mu_{84}) \quad (11)$$

$$W_i = L_i(\mu_v) + \frac{1}{2!}\Delta\mu_{ai} L_i'(\mu_v) + \ldots \quad (12)$$

$$B_i(\mu_{ai}) = \int_0^\infty L_i(\mu_a) d\mu_a \quad (13)$$

$$B = \sum_{i=1}^N B_i \quad (14)$$

$$L = \langle l \rangle = \sum_{i=1}^N L_i$$

$$= \frac{\int_0^\infty ls(t)\exp\left[-\sum_{i=1}^N (\mu_{ai} l_i)\right] dt}{\int_0^\infty s(t)\exp\left[-\sum_{i=1}^N (\mu_{ai} l_i)\right] dt} \quad (15)$$

[In Eqs (9) to (15), C indicates the fixed absorption coefficient of the imaginary medium, $\Delta\mu_{ai}$ the absorption coefficient deviation of $\mu_{al}$ from $\mu_v$, Bi ($\mu_{ai}$) the attenuation amount in each voxel i about the time integral I of the impulse response h(t) of the measured medium, Bi ($\mu_v$) the attenuation amount about the time integral I of the impulse response of the imaginary medium with the absorption coefficient being $\mu_v$ (provided that this I is equal to a value resulting when $\mu_{ai} = \mu_v$ in Eq (6)), ΔBi ($\mu_{ai}$) the attenuation amount deviation of Bi ($\mu_{ai}$) from Bi ($\mu_v$), Li($\mu_v$) the mean path length in voxel i of the imaginary medium with the absorption coefficient being $\mu_v$ (the mean path length about the time integral I, this Li ($\mu_v$) being equal to a value resulting when $\mu_{ai} = \mu_v$ in Eq (7)), which is equal to the weighted mean of the time-resolved path length li in voxel i, Wi the weight function for the attenuation amount deviation ΔBi($\mu_{ai}$), which is represented by a function of the absorption coefficient deviation $\Delta\mu_{al}$ and first-order and higher-order partial differential coefficients (L, L', L", . . . ).]

Here the first-order and higher-order partial differential coefficients can be directly calculated from the time-resolved waveform determined for the imaginary medium.

The absorption coefficient distribution can also be quantitatively measured by using other various quantities derived according to the various optical CT in addition to the above-stated measuring methods; for example, it can be measured by using a combination of the difference of mean path length with the weight function corresponding to the dispersion of path length, because a relation similar to above Eq (9) also holds between the difference of mean path length and the weight function corresponding to the path length dispersion. Specifically, this measurement is performed for light of different wavelengths and a concentration distribution of an absorptive constituent (absolute value) is quantitatively determined from the resultant absorption coefficients and the extinction coefficients specific to the substance.

2. Method of calculating time-resolved path length

Next, let us derive an equation for calculating the time-resolved path lengths li which are the elements of the time-resolved photon path distribution [li], for the imaginary medium described by the finite grid model 10.

Since it is feasible to calculate the various weight functions corresponding to the measuring methods used in optical CT of the TIS (time-resolved integral spectroscopy), TGS (time-resolved gating integral spectroscopy), and PMS (phase modulation spectroscopy), from the time-resolved path length li, specific examples of these will also be described.

The voxel i of the measured medium has the absorption coefficient $\mu_{ai}$, while the voxel i of the finite grid model 10 of the imaginary medium has the absorption coefficient $\mu_{ai}=0$. In this case, the impulse response h(t) of the finite grid model 10 of the imaginary medium shown in FIG. 1 can be expressed as follows by substituting $\mu_{ai}=0$ into Eq (3).

$$h(t)=s(t) \quad (1.1)$$

Namely, the impulse response s(t) of the imaginary medium detected at the light detection position q is equal to the impulse response h(t) of the measured medium detected at the light detection position q where the measured medium is assumed to be nonabsorbing.

At this time, the relation between the time-resolved path length li and the path length l can be expressed by the following equation.

$$\sum_{i=1}^{N} l_i(t) = l(t) \quad (2.1)$$

[In the equation, i indicates each of numbers i (i=1, 2, ..., N; 1≦N)) of the voxels constituting the finite grid model 10.]

The above relation between the time-resolved path length li and the path length l also holds even in the case where a photon travels in a zigzag path to pass an identical voxel twice or more times. In the above equation, the total path length l and the time-resolved path length li of each voxel i are represented by "l(t)" and "li(t)," respectively, in order to explicitly express that they are functions of time t.

The following will detail the principle and the process of calculating the time-resolved path length li of voxel i, using such t as a parametric variable.

FIG. 2 is a schematic illustration showing the paths and probability density of an ensemble of photons having passed the voxel i among an ensemble of photons constituting the impulse response s(t) and having the path length of l (i.e., an ensemble of photons detected at a point of time t), in the case where propagating light is detected at the light detection position q after injection of impulse light A at the light injection position p on the imaginary medium described by the finite grid model 10 shown in FIG. 1, and the value Upiq(t) of such an ensemble of photons detected at the point of time t at the light detection position q.

In the finite grid model 10, where propagating light is detected at the light detection position q after injection of the pulse light A at the light injection position p, let us consider a photon existence probability density Ui(t',t) that an ensemble of photons constituting the impulse response s(t) and having the path length of l (i.e., an ensemble of photons detected at the point of time t) exists in voxel i at a point of time t' (0≦t'≦t) before the detection at the light detection position q. In the following description, this photon existence probability density Ui(t',t) will be referred to simply as "photon existence probability density Ui(t',t) in voxel i at time t'."

At this time, the photon existence probability density Ui(t',t) in voxel i at time t', described by introducing the aforementioned new time variable t', can be expressed like the following equation by applying the reciprocity theorem.

$$U_i(t',t)=U_{pi}(t')U_{qi}(t-t') \quad (2.2)$$

[In the equation, Upi(t') indicates a photon existence probability density that photons injected at the light injection position p at time t'=0 exist in voxel i at time t'=t', Uqi(t-t') indicates a photon existence probability density that photons injected at the light detection position q at time t-t'=0 exist in voxel i at time t-t'.]

In the scattering media like living tissue, the reciprocity theorem approximately holds for injection of collimated light and injection of a pencil beam. For applying the reciprocity theorem more precisely, it is preferable to utilize a light injection method called isotropic light injection. This is because the reciprocity theorem holds more accurately in the isotropic light injection method. This isotropic light injection method is a light injection method reported by the Inventor, which is disclosed, for example, in Japanese Patent Application No. 5-301979 and Y. Tsuchiya, K. Ohta, and T. Urakami: Jpn. J. Appl. Phys. 34, Part 1, pp. 2495–2501 (1995).

In the following description, Upi(t') and Uqi(t-t') in above Eq (2.2) will be referred to simply as "photon existence probability density Upi(t') in voxel i at time t'" and as "photon existence probability density Uqi(t-t') in voxel i at time t-t'," respectively.

Figure 3:
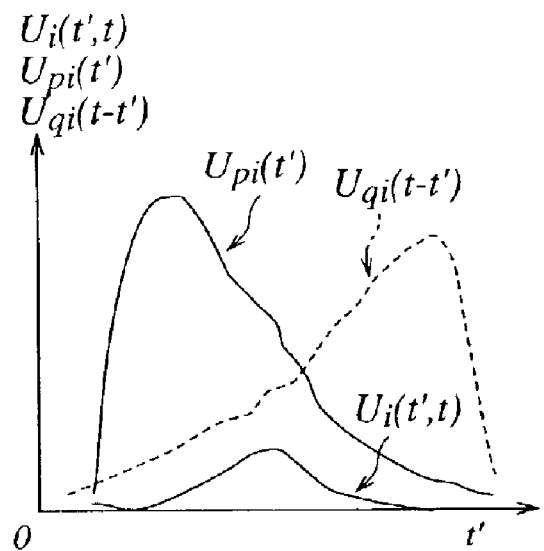
FIG. 3 is a graph showing an example of temporal waveforms of the photon existence probability density $U_i(t',t)$ in voxel i at the time t', the photon existence probability density $U_{pi}(t')$ in voxel i at the time t', and the photon existence probability density $U_{qi}(t-t')$ in voxel i at the time t' in the finite grid model shown in FIG. 2.

FIG. 3 is a graph showing an example of the photon existence probability density Ui(t',t) in voxel i at time t' in the finite grid model 10, represented by above Eq (2.2), the photon existence probability density Upi(t') in voxel i at time t', and the photon existence probability density Uqi(t-t') in voxel i at time t-t'.

Above Ui(t',t) can be determined by calculating the two forward problems indicated by Eq (2.2). At this time, Upi(t') can be calculated with injection of the impulse light A at the light injection position p on the finite grid model 10. Uqi(t-t') can also be calculated with injection of the impulse light A at the light detection position q on the finite grid model 10. For specific calculation of the above forward problems, it is possible to apply the Monte Carlo calculation, the numerical calculation of Path Integral or the transport equation, the numerical calculation of the photon diffusion equation, and so on. On this occasion, since the finite grid model 10 is nonabsorbing, the calculation algorithm becomes simpler than the calculation of forward problems in the conventional absorbing case, so that the calculation time also becomes shorter.

By calculating the aforementioned photon existence probability density Ui(t',t) in voxel i at time t', it is feasible to calculate according to the equation below, the probability density Ui(t) that an ensemble of photons with the path length of l constituting the impulse response s(t) detected at the point of time t at the light detection position q after injection of the impulse light A at the light injection position p into the finite grid model 10 exists in voxel i during the period of 0≦t'≦t in which photons travel from the light injection position p to the light detection position q in the finite grid model 10. This probability density Ui(t) is accumulation of probabilities including one that a photon traveling in a zigzag path in the finite grid model 10 (in the imaginary medium or in the measured medium) has existed in an identical voxel at different times.

$$\int_0^t U_i(t', t) dt' = U_i(t) \quad (2.3)$$

Ui(t) represented by above Eq (2.3) indicates a photon existence cumulative probability in voxel i of an ensemble of photons constituting the impulse response s(t) and having the path length of l, and in the following description, it will be referred to simply as "photon existence cumulative probability Ui(t) in voxel i during the period 0≦t'≦t."

Here the summation of the photon existence cumulative probability Ui(t) represented by Eq (2.3), over all voxels in the finite grid model 10 provides a photon existence cumulative probability U(t) in the finite grid model 10 to yield the following equation.

$$\sum_{i=1}^{N}\int_{0}^{t}U_{i}(t',t)dt' = \sum_{i=1}^{N}U_{i}(t) = U(t) \qquad (2.4)$$

This photon existence cumulative probability U(t) indicates a cumulative probability that an ensemble of photons with the path length of l constituting the impulse response s(t) detected at the point of time t at the light detection position q after injection of the impulse light A at the light injection position p into the finite grid model 10 exists in the finite grid model 10 (in all the voxels) during the period 0≦t'≦t in which the photons travel in the finite grid model 10 from the light injection position p to the light detection position q.

In the following description, U(t) represented by above Eq (2.4) will be referred to as "photon existence cumulative probability U(t) in all voxels during period 0≦t'≦t."

On the other hand, against the aforementioned photon existence probability density Ui(t',t) in voxel i at time t', let us consider a probability density Upq(t',t) that an ensemble of photons with the path length of l constituting the impulse response s(t) detected at the point of time t at the light detection position q after injection of the impulse light A at the light injection position p into the finite grid model 10 exists in the finite grid model 10 (in the imaginary medium) at the point of time t' (0≦t'≦t) prior to the detection at the light detection position q. Namely, let us consider a "photon existence probability density Upq(t',t) in all voxels at time t'," against the "photon existence probability density Ui(t',t) in voxel i at time t'." In this case, since consideration is given to the photon existence probability density at time t', the summation of photon existence probability densities over all voxels is equal to Upq(t',t) and this Upq(t',t) can be expressed by the following equation using Ui(t',t).

$$U_{pq}(t',t) = \sum_{i=1}^{N}U_{i}(t',t) \qquad (2.5)$$

The definite integral of this Eq (2.5) over the range from the time t'=0 to the time t'=t is naturally equal to the previously obtained photon existence cumulative probability U(t) in all the voxels during the period 0≦t'≦t, and can be expressed by the following equation.

$$U(t) = \int_{0}^{t}U_{pq}(t',t)dt' \qquad (2.6)$$

Since the nonabsorbing imaginary medium is assumed in the method of calculating the photon path distribution inside the scattering medium according to the present invention herein, the photon existence probability density Upq(t',t) in all voxels at time t' is constant from the time t'=0 to time t'=t. Then the cumulative probability U(t) can be expressed like the following equation using Eq (2.6).

$$U(t) = tU_{pq}(t',t) \qquad (2.7)$$

In addition to the above fact, since the photon existence probability density Upq(t',t) in all voxels at time t' in the nonabsorbing imaginary medium is constant from the time t'=0 to the time t'=t, it is understood that this Upq(t',t) is equal to the impulse response detected at the point of time t at the light detection position q, i.e., s(t) defined in Eq (1.1). Namely, the relationship between Upq(t',t) and s(t) is expressed like the following equation.

$$s(t) = U_{pq}(t',t) \qquad (2.8)$$

From the above, the photon existence cumulative probability U(t) in all voxels during period 0≦t'≦t in Eq (2.4) is eventually expressed by the following equation, by substituting the result of Eq (2.8) into Eq (2.7).

$$U(t) = ts(t) \qquad (2.9)$$

Further, it is understood that the summation of aforementioned Upiq(t) described with FIG. 2, over all voxels is equal to the photon existence cumulative probability U(t) in the finite grid model 10 and the relationship indicated by the following equation holds.

$$\sum_{i=1}^{N}U_{piq}(t) = \sum_{i=1}^{N}U_{i}(t) = U(t) \qquad (2.10)$$

Figure 4:
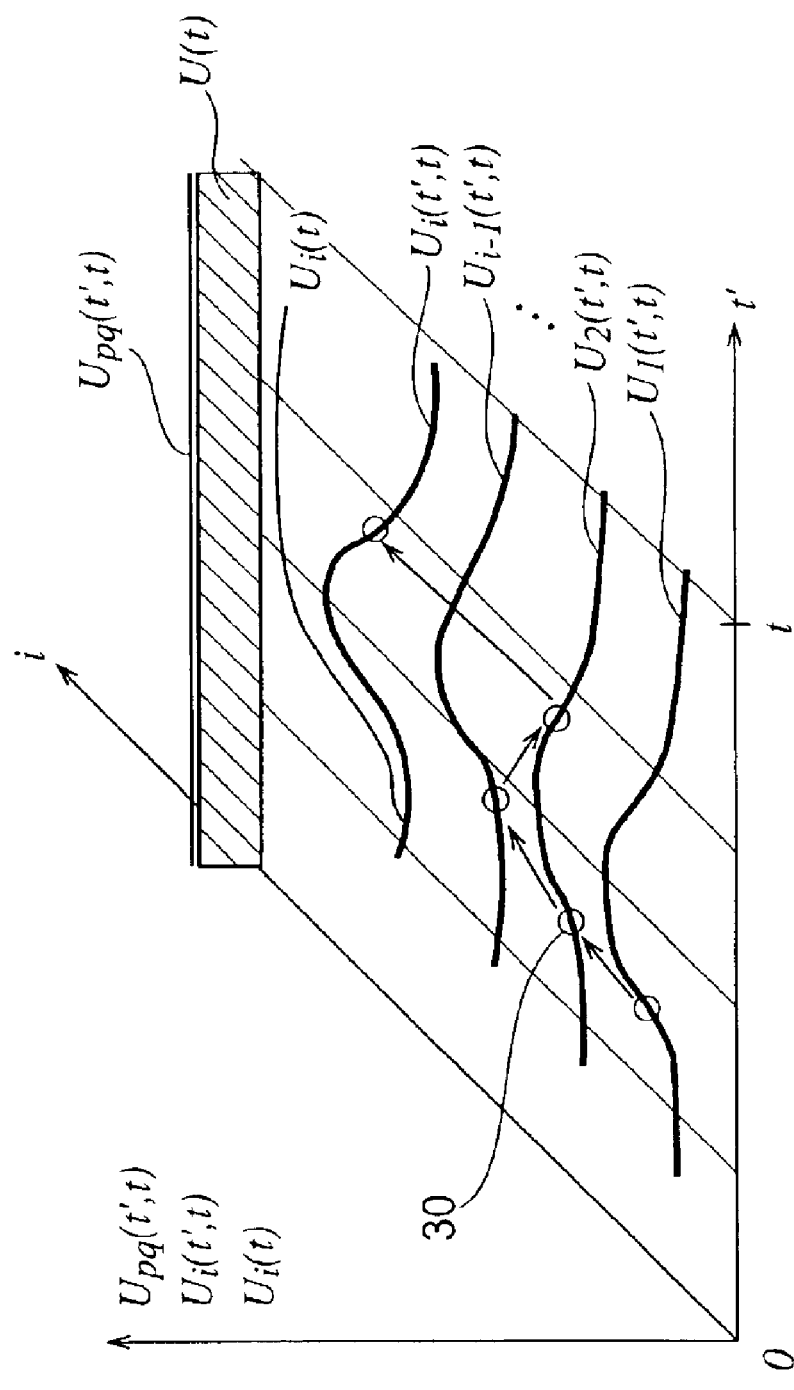
FIG. 4 is a graph schematically showing the relationship among the photon existence cumulative probability $U_i(t)$ in voxel i in the duration of 0≦t'≦t, the photon existence probability density $U_i(t',t)$ in voxel i at the time t', and the photon existence probability density Upq(t',t) in all the voxels at the time t'.

FIG. 4 schematically shows the relationship among the aforementioned photon existence cumulative probability Ui(t) in voxel i during period 0≦t'≦t, the photon existence probability density Ui(t',t) in voxel i at time t', and the photon existence probability density Upq(t',t) in all voxels at time t'. Here reference numeral 30 in FIG. 4 designates a photon.

Let li(t',t) be the time-resolved path length in voxel i at time t' of an ensemble of photons with the path length of l among photons constituting the impulse response s(t) detected at the point of time t at the light detection position q after injection of the pulse light A at the light injection position p into the finite grid model 10. Then the integral of this li(t',t) from the time t'=0 to the time t'=t is equal to the time-resolved path length li(t) and can be expressed by the following equation.

$$\int_{0}^{t}li(t',t)dt' = l_{i}(t) \qquad (2.11)$$

Incidentally, since the speed of photons in the finite grid model 10 is constant, the path length is always proportional to the photon existence probability at an arbitrary time or an arbitrary portion.

Specifically, when focus is placed on an ensemble of photons with the path length of l among photons constituting the impulse response s(t) detected at the point of time t at the light detection position q after injection of the impulse light A at the light injection position p into the finite grid model 10, the time-resolved path length li(t',t) in voxel i at an arbitrary time t' is proportional to the photon existence probability density Ui(t',t) in voxel i at the time t'. Then the time-resolved path length li(t), which is the time integral of li(t',t), is also proportional to the photon existence cumulative probability Ui(t) which is the time integral of Ui(t',t). Further, when focus is placed on an ensemble of photons with the path length of l among photons constituting the impulse response s(t) detected at the point of time t at the light detection position q after injection of the impulse light A at the light injection position p into the finite grid model 10, the path length l is proportional to the photon existence cumulative probability U(t).

By letting A be a constant of the proportionality, the following equation can be yielded from the relations of Eq (2.1), Eq (2.9), and Eq (2.11).

$$A = \frac{l_i(t', t)}{U_i(t', t)} = \frac{l_i(t)}{U_i(t)} = \frac{\sum_{i=1}^{N} l_i(t)}{\sum_{i=1}^{N} U_i(t)} = \frac{l(t)}{U(t)} = \frac{l(t)}{ts(t)} = \frac{c}{s(t)} \quad (2.12)$$

[In the equation, c is the speed of photons traveling in the medium.]

By performing equivalent deformation of the relation of Eq (2.12) and solving it with respect to the time-resolved path length li(t), we obtain the following equation.

$$l_i(t) = \frac{U_i(t)}{U(t)} l(t) = \frac{U_i(t)}{ts(t)} l(t) = \frac{c}{s(t)} U_i(t) \quad (2.13)$$

From this Eq (2.13), the elements expressing the time-resolved photon path distribution as the N-dimensional vector [li], i.e., the time-resolved path length li for each voxel can be calculated by determining Ui(t',t) by calculating the forward problems indicated by Eq (2.2) and further using Ui(t) calculated from this Ui(t',t), U(t), and, l determined as l=ct by given time t, or s(t).

The time-resolved path length li is directly used in the time-resolved optical CT image reconstruction making use of the time-resolved response. This is because the weight function in time-resolved optical CT is equal to the time-resolved path length li. As described hereinafter, the time-resolved path length li is the base quantity for describing the weight functions in the various measuring methods.

3. Specific calculation methods of time-resolved path length li

Figure 5:
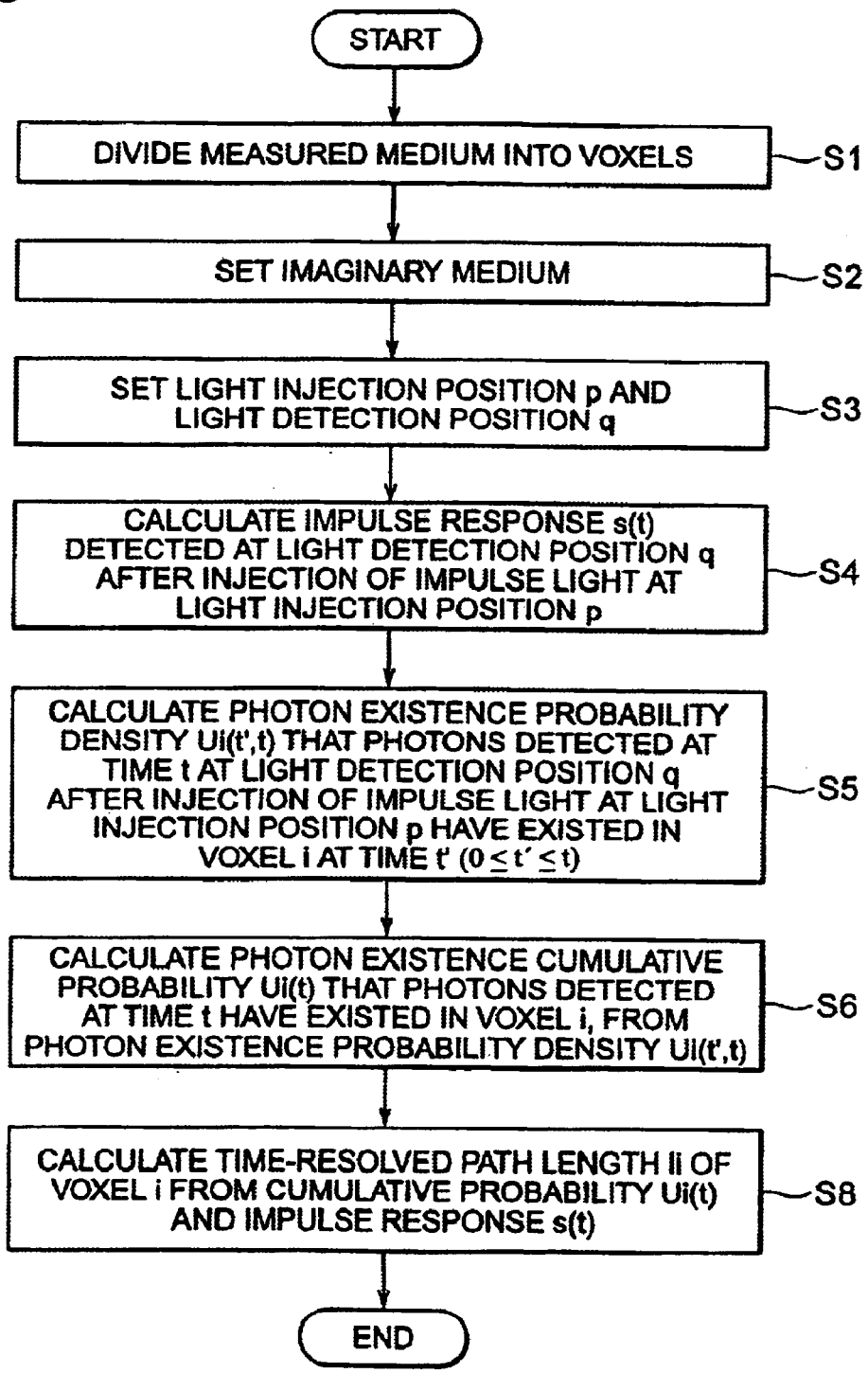
FIG. 5 is a flowchart showing an embodiment of the method of calculating the photon path distribution inside the scattering medium according to the present invention.

FIG. 5 is a flowchart showing an embodiment of the method of calculating the photon path distribution inside the scattering medium according to the present invention. The following will describe the flowchart shown in FIG. 5.

The first step is to divide the measured medium as a scattering medium into N (1≦N) voxels each having a predetermined size and assumed to have a uniform absorption distribution in a measurement wavelength region (S1).

The second step is to hypothesize an imaginary medium that can be assumed to have the same shape, boundary conditions, and scattering distribution as the measured medium, have a uniform refractive index distribution, and be nonabsorbing, for the measured medium divided into the N voxels (S2).

The third step is to set, on a surface of the imaginary medium, a light injection position p for injection of impulse light A, and a light detection position q for detection of an impulse response s(t) at a time t of the impulse light A having been injected at the light injection position p and having propagated in the imaginary medium (S3).

The fourth step is to calculate the impulse response s(t) detected at the light detection position after injection of the impulse light A at the light injection position p into the imaginary medium (S4).

The next step is to calculate the photon existence probability density Upi(t') that, after injection of the impulse light A at the light injection position p into the imaginary medium, photons injected at the light injection position p at the time t'=0 exist in voxel i at the time t'=t'. Subsequently calculated is the photon existence probability density Uqi (t−t') that, after injection of the impulse light A at the light detection position q into the imaginary medium, photons injected at the light detection position p at the time t−t'=0 exist in voxel i at the time t−t'. Then calculated according to Eq (2.2) is the photon existence probability density Ui(t',t) that, after injection of the impulse light A at the light injection position p into the finite grid model 10, an ensemble of photons with the path length of l constituting the impulse response s(t) detected at the point of time t at the light detection position exists in voxel i at the point of time t' (0≦t'≦t) prior to the detection at the light detection position (S5).

In the above case, the photon existence probability densities in all the voxels constituting the finite grid model 10 can be calculated in parallel or simultaneously for one light injection position. For this reason, there is no need for the conventional time-consuming calculation of varying the absorption coefficient of each voxel and repeatedly solving the forward problems by the number of times equal to the total number N of voxels, which extremely decreases the calculation time.

The next step is to calculate the photon existence cumulative probability Ui(t) that the ensemble of photons constituting the impulse response s(t) detected at the point of time t at the light detection position q has existed in voxel i, from the photon existence probability density Ui(t',t) according to Eq (2.3) (S6).

The last step is to calculate the time-resolved path length li in voxel i, using the photon existence cumulative probability Ui(t) and the impulse response s(t) according to Eq (2.13) (S8).

As described in the first embodiment of the present invention above, the method of calculating the photon path distribution inside the scattering medium according to the present invention is configured to solve the forward problems indicated by Eq (2.2) for the imaginary medium assumed to have the same scattering characteristics and boundary conditions as the measured medium, and be nonabsorbing, and thus the calculation time thereof becomes shorter than in the conventional absorbing case of computation of forward problems. Further, it obviates the need for the conventional time-consuming problem calculation of varying the absorption coefficient of each voxel and repeatedly solving the forward problems by the number of times equal to the total number of voxels, and permits direct and quick calculation of the time-resolved path length li in voxel i.

When the above method of calculating the photon path distribution inside the scattering medium is applied to the optical CT using various light responses, the weight function Wi corresponding to the predetermined measuring method for quantitatively measuring the concentration distribution of the absorptive constituent inside the measured medium is calculated using the time-resolved path length li calculated for each arbitrary voxel i of the imaginary medium in the last stage of the flowchart shown in FIG. 5. In this case, there are a method of directly calculating the weight function Wi corresponding to the predetermined measuring method from the time-resolved path length li calculated for each arbitrary voxel i of the imaginary medium; and a method of first determining the weighted mean Li for time of the time-resolved path length li calculated for each arbitrary voxel i of the imaginary medium and then calculating the weight function Wi corresponding to the predetermined measuring method using the weighted mean Li.

As also described previously, there was no conventionally known specific calculation method of the time-resolved path length li and, therefore, there was no idea proposed on the method of first determining the time-resolved path length li and thereafter calculating the weighted mean Li of the time-resolved path length li and the weight function Wi. In contrast to it, since the calculation methods of the weight function herein are based on the quick and direct calculation of the time-resolved path length li of voxel i, they permit quick calculation of the weighted mean Li of the time-resolved path length li or the weight function Wi corresponding to each of the various predetermined specific measuring methods for quantitatively measuring the concentration distribution of the absorptive constituent in the measured medium, using the time-resolved path length li. Specific calculation methods of the weight functions corresponding to optical CT using various light responses, using the time-resolved path length li calculated for each arbitrary voxel i of the imaginary medium will be described later.

Figure 6:
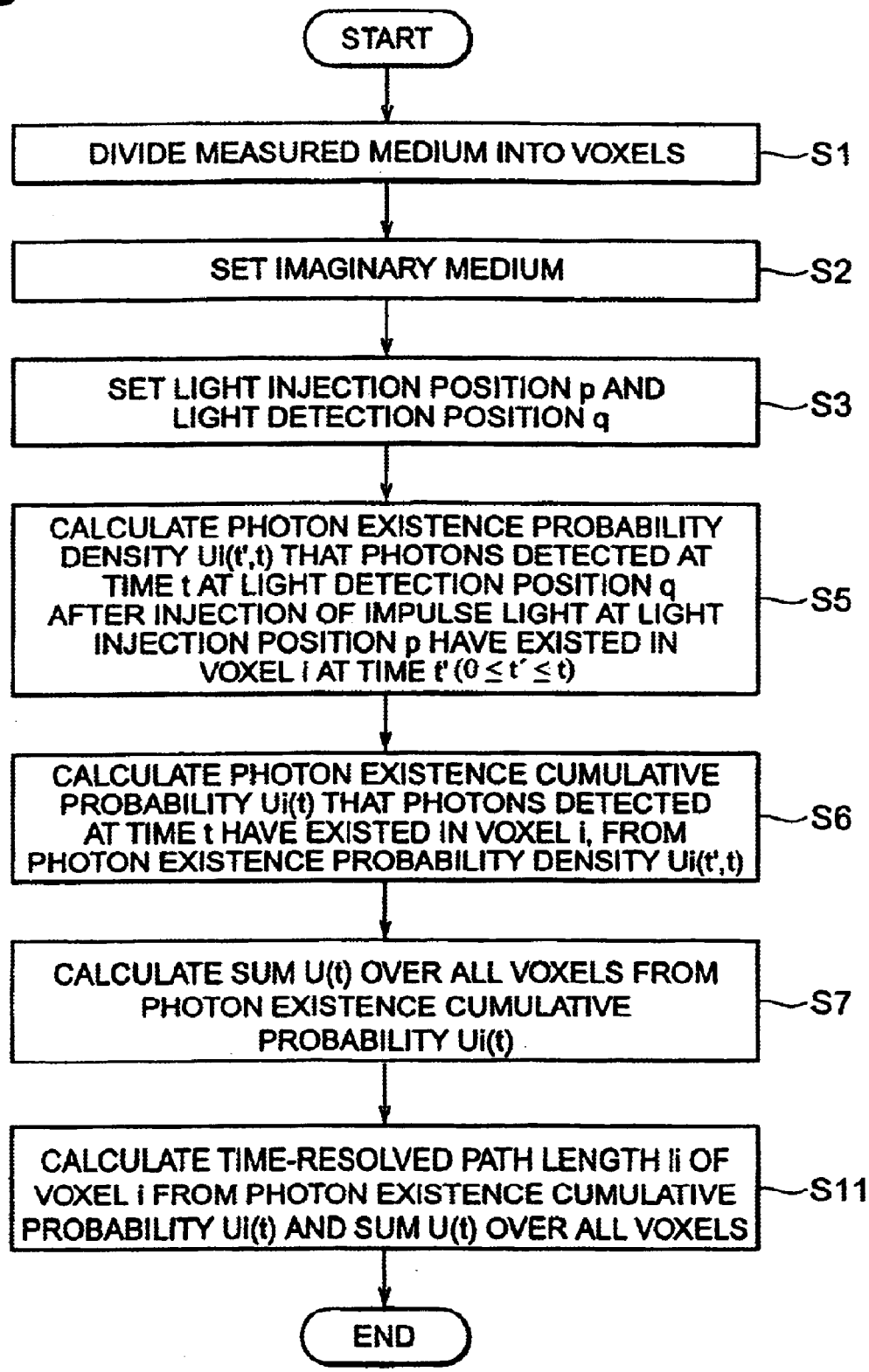
FIG. 6 is a flowchart showing a second embodiment of the method of calculating the photon path distribution inside the scattering medium according to the present invention.

FIG. 6 is a flowchart showing a second embodiment of the method of calculating the photon path distribution inside the scattering medium according to the present invention. The following will describe the flowchart shown in FIG. 6.

The first step is to divide the measured medium as a scattering medium into N ($1 \leq N$) voxels each having a predetermined size and assumed to have a uniform absorption distribution, in the measurement wavelength region (S1).

The second step is to hypothesize an imaginary medium that can be assumed to have the same shape, boundary conditions, and scattering distribution as the measured medium, have a uniform refractive index distribution, and be nonabsorbing, for the measured medium divided into the N voxels (S2).

The third step is to set, on a surface of the imaginary medium, a light injection position p for injection of impulse light A, and a light detection position q for detection of the impulse response s(t) at the time t of the impulse light A having been injected at the light injection position p and having propagated in the imaginary medium (S3).

The next step is to calculate the photon existence probability density Upi(t') that, after injection of the impulse light A at the light injection position p into the imaginary medium, photons injected at the light injection position p at the time t'=0 exist in voxel i at the time t'=t'. Subsequently calculated is the photon existence probability density Uqi (t–t') that, after injection of the impulse light A at the light detection position q into the imaginary medium, photons injected at the light detection position p at the time t–t'=0 exist in voxel i at the time t–t'. Then calculated according to Eq (2.2) is the photon existence probability density Ui(t',t) that, after injection of the impulse light A at the light injection position p into the finite grid model 10, an ensemble of photons with the path length of l constituting the impulse response s(t) detected at the point of time t at the light detection position exist in voxel i at the point of time t' ($0 \leq t' \leq t$) prior to the detection at the light detection position (S5).

In the above case, the photon existence probability densities in all the voxels constituting the finite grid model 10 can also be calculated in parallel or simultaneously for one light injection position. For this reason, there is no need for the conventional time-consuming calculation of varying the absorption coefficient of each voxel and repeatedly solving the forward problems by the number of times equal to the total number N of voxels, which extremely decreases the calculation time.

The next step is to calculate the photon existence cumulative probability Ui(t) that the ensemble of photons constituting the impulse response s(t) detected at the point of time t at the light detection position q has existed in voxel i, from the photon existence probability density Ui(t',t) according to Eq (2.3) (S6).

The next step is to calculate a sum U(t) of the photon existence cumulative probabilities Ui(t) for all the voxels according to Eq (2.4) (S7).

The last step is to calculate the time-resolved path length li in voxel i, using the photon existence cumulative probability Ui(t) and the sum U(t) over all the voxels according to Eq (2.13) (S11).

It is seen from the above description of the second embodiment of the present invention, as in the description of the first embodiment of the present invention described previously, that the method of calculating the photon path distribution inside the scattering medium according to the present invention is configured to solve the forward problems indicated by Eq (2.2) for the imaginary medium assumed to have the same scattering characteristics and boundary conditions as the measured medium and be non-absorbing and thus the calculation time thereof becomes shorter than in the conventional absorbing case of computation of forward problems. It is further seen that it obviates the need for the conventional time-consuming problem calculation of varying the absorption coefficient of each voxel and repeatedly solving the forward problems by the number of times equal to the total number of voxels and thus permits direct and quick calculation of the time-resolved path length li in voxel i.

When the above method of calculating the photon path distribution inside the scattering medium is applied to the optical CT using various light responses, as in the first embodiment of the present invention described previously, the weight function Wi corresponding to the predetermined measuring method for quantitatively measuring the concentration distribution of the absorptive constituent inside the measured medium is calculated using the time-resolved path length li calculated for each arbitrary voxel i of the imaginary medium in the last stage of the flowchart shown in FIG. 6. In this case, there are also the method of directly calculating the weight function Wi corresponding to the predetermined measuring method from the time-resolved path length li calculated for each arbitrary voxel i of the imaginary medium; and the method of first determining the weighted mean Li for time of the time-resolved path length li calculated for each arbitrary voxel i of the imaginary medium and then calculating the weight function Wi corresponding to the predetermined measuring method using the weighted mean Li.

Since the calculation methods of weight function are based on the quick and direct calculation of the time-resolved path length li of voxel i, they permit quick calculation of the weighted mean Li of the time-resolved path length li or the weight function Wi corresponding to each of the various predetermined specific measuring methods for quantitatively measuring the concentration distribution of the absorptive constituent inside the measured medium, using the time-resolved path length li.

As described above, the methods of calculating the photon path distribution inside the scattering medium according to the present invention can be applied to the optical CT using various light responses. In this case, the weight function Wi corresponding to the predetermined measuring method for quantitatively measuring the concentration distribution of the absorptive constituent inside the measured medium is calculated using the time-resolved path length li calculated for each arbitrary voxel i of the imaginary medium, in the last stage of the flowchart shown in FIG. 5 or in FIG. 6.

For example, specific examples include the time-resolved spectroscopy (TIS), the time-resolved gating integral spectroscopy (TGS), the phase modulation spectroscopy in the frequency domain (PMS), the average value method (TIS), etc. derived based on the MBL by the Inventor and others. In these cases, various light responses are defined by mathematical conversion of the aforementioned impulse response, and the optical CT processes corresponding to the respective methods employ their respective weight functions different from each other.

The following will describe examples of application of the time-resolved path length li determined by the method of calculating the photon path distribution inside the scattering medium according to the present invention to the optical CT using the light responses in the time-resolved spectroscopy (TIS), the time-resolved gating integral spectroscopy (TGS), the phase modulation spectroscopy in the frequency domain (PMS), and so on.

4. Photon path distribution inside scattering medium and weight function in TIS

As described previously, the optical CT based on TIS using the time integral I of the impulse response h(t) employs the weight function described using the mean path length Li of voxel i or the path length dispersion or the like for the impulse response h(t). This weight function Wi is defined as a weight function for a reference medium with a uniform absorption distribution.

First, let us consider the time integral I of the impulse response h(t) of a scattering medium with a heterogeneous absorption distribution. A model considered herein is one obtained by setting the absorption coefficient of voxel i of the imaginary medium described by the finite grid model 10 shown in FIG. 1, as $\mu_{ai}$. Using these, the time integral I of the impulse response h(t) is given by the following equation.

$$\ln I = \ln \int_0^\infty s(t)dt - \sum_{i=1}^N \int_0^{\mu_{ai}} L_i(\mu_a)d\mu_a \qquad (4.1)$$

[In the equation, $\mu_{ai}$ indicates the absorption coefficient of voxel i, s(t) indicates the impulse response h(t) detected at the detection position on the assumption that the measured medium is nonabsorbing, and Li indicates the mean path length in voxel i (weighted mean of time-resolved path length li in voxel i) of an ensemble of photons constituting the time integral I detected at the detection position.]

In this equation, lnI is described as separated into the term independent of absorption and the term dependent upon the absorption coefficient $\mu_{ai}$ of each voxel (attenuation).

Here the mean path length Li of voxel i is a quantity dependent upon the scattering characteristics, boundary conditions, and absorption and absorption distribution of the scattering medium, and is given by the following equation.

$$\frac{\partial \ln I}{\partial \mu_{ai}} = \frac{1}{I}\frac{\partial I}{\partial \mu_{ai}} = \frac{\int_0^\infty l_i s(t)\exp\left[-\sum_{i=1}^N (\mu_{ai} l_i)\right]dt}{\int_0^\infty s(t)\exp\left[-\sum_{i=1}^N (\mu_{ai} l_i)\right]dt} = -L_i \qquad (4.2)$$

The weight function Wi used in the corresponding optical CT is defined for the imaginary medium with the uniform absorption coefficient $\mu_v$, and is given by the following equation. A model in this case is one obtained by setting the absorption coefficient of voxel i in the model shown in FIG. 1, as $\mu_v$.

$$W_i = L_i(\mu_v) + \frac{1}{2!}\Delta\mu_{ai} L_i'(\mu_v) + \ldots \qquad (4.3)$$

$$\Delta\mu_{ai} = \mu_{ai} - \mu_v \qquad (4.4)$$

$$L(\mu_v) = \sum_{i=1}^N L_i(\mu_v) \qquad (4.5)$$

$$L_i(\mu_v) = \frac{\int_0^\infty l_i s(t)\exp[-\mu_v l]dt}{\int_0^\infty s(t)\exp[-\mu_v l]dt} \qquad (4.6)$$

[In Eqs (4.3) to (4.6), $\mu_v$ indicates the constant absorption coefficient given to the imaginary medium, $\Delta\mu_{ai}$ the absorption coefficient deviation of $\mu_{ai}$ from $\mu_v$, Li ($\mu_v$) the mean path length in voxel i (weighted mean of time-resolved path length li in voxel i) of the imaginary medium with the constant absorption coefficient $\mu_v$, L ($\mu_v$) the mean path length of the impulse response h(t) of the imaginary medium with the constant absorption coefficient $\mu_v$ (the weighted mean of the path length l in the imaginary medium with the absorption coefficient $\mu_v$), and Wi the weight function for the attenuation amount deviation $\Delta B_i$ ($\mu_{ai}$) in aforementioned Eq (9), which is represented by a function of the absorption coefficient deviation $\Delta\mu_{ai}$ and the first-order and higher-order partial differential coefficients (L, L', L", . . . ).]

Here the first-order and higher-order partial differential coefficients can be directly calculated from the time-resolved waveform obtained for the imaginary medium.

5. Photon path distribution inside scattering medium and weight function in TGS

First, a time-resolved gating integral signal Ig of the impulse response h(t) of a scattering medium with a heterogeneous absorption distribution is given by the following equation.

$$\ln I_g = \ln \int_{t_1}^{t_2} s(t)dt - \sum_{i=1}^N \int_0^{\mu_{ai}} L_{gi}(\mu_a)d\mu_a \qquad (5.1)$$

[In the equation, $L_{gi}$ indicates a mean path length in voxel i (weighted mean of time-resolved path length li in a gate time in voxel i) of an ensemble of photons constituting the time gating integral Ig of the impulse response h(t).]

Here the time range of the gating integration is [t1,t2], and by setting it as [0, ∞], the gating integral yields the time integral signal I of the impulse response h(t) obtained in the previous section.

The weight function Wgi used in the corresponding optical CT is defined for the imaginary medium with the uniform absorption coefficient $\mu_v$, and is given by the following equation.

$$W_{gi} = L_{qi}(\mu_v) + \frac{1}{2!}\Delta\mu_{ai} L_{gi}'(\mu_v) + \ldots \qquad (5.2)$$

$$L_g(\mu_v) = \sum_{i=1}^N L_{gi}(\mu_v) \qquad (5.3)$$

$$L_{gi}(\mu_v) = \frac{\int_{t_1}^{t_2} l_i s(t)\exp[-\mu_v l]dt}{\int_{t_1}^{t_2} s(t)\exp[-\mu_v l]dt} \qquad (5.4)$$

[In Eqs (5.2) to (5.4), $\mu_v$ indicates the constant absorption coefficient given to the imaginary medium, $\Delta\mu_{ai}$ indicates the absorption coefficient deviation of $\mu_{ai}$ from $\mu_v$, as presented in aforementioned Eq (4.4), Lgi ($\mu_v$) indicates the mean path length in voxel i (weighted mean of time-resolved path length li in gating time in voxel i) of an ensemble of photons constituting the time gating integral Ig of the impulse response h(t) of the imaginary medium, Lg ($\mu_v$) indicates the mean path length (weighted mean) of an ensemble of photons constituting the time gating integral Ig of the impulse response h(t) of the imaginary medium given the constant absorption coefficient $\mu_v$, and Wi indicates the weight function for the attenuation amount deviation $\Delta$Bgi ($\mu_{ai}$) in application of the attenuation amount deviation $\Delta$Bi ($\mu_{ai}$) in aforementioned Eq (9) to TGS, which is represented by a function of the absorption coefficient deviation $\Delta\mu_{ai}$ and the first-order and higher-order partial differential coefficients (Lg, Lg', Lg", ... ).]

6. Photon path distribution inside scattering medium and weight function in PMS

For a scattering medium with a heterogeneous absorption distribution, a response obtained in PMS is the Fourier transform of the impulse response h(t) for the scattering medium with the heterogeneous absorption distribution and is given by the following equation.

$$H(\omega) = \int_0^\infty s(t)\exp(-b)\exp(-j\omega t)dt \qquad (6.1)$$
$$= R(b, \omega) + jX(b, \omega)$$
$$= A(b, \omega)\exp[-j\phi(b, \omega)]$$

$$b = \sum_{i=1}^N (\mu_{ai} l_i) = \sum_{i=1}^N (\mu_{ai} c t_i) \qquad (6.2)$$

Here R, X, A, and $\phi$ are defined as follows.

$$R = \int_0^\infty s(t)\exp\left[-\sum_{i=1}^N (\mu_{ai} c t_i)\right]\cos\omega t\, dt \qquad (6.3)$$

$$X = -\int_0^\infty s(t)\exp\left[-\sum_{i=1}^N (\mu_{ai} c t_i)\right]\sin\omega t\, dt \qquad (6.4)$$

$$A = (R^2 + X^2)^{1/2} \qquad (6.5)$$

$$\phi = -\tan^{-1}\frac{X}{R} \qquad (6.6)$$

[In Eqs (6.1) to (6.6), R and X indicate the real part and the imaginary part, respectively, and A and $\phi$ indicate the amplitude and phase delay, respectively.

R, X, A, and $\phi$ can be readily measured by a lock-in amplifier or the like.

Since the relations (6.7) to (6.10) below hold, R, X, A, and $\phi$ can be written as in Eqs (6.11) to (6.14).

$$\frac{\partial R_i}{\partial \omega} \equiv -\int_0^\infty t_i s(t)\exp\left[-\sum_{i=1}^N (\mu_{ai} c t_i)\right]\sin\omega t\, dt \qquad (6.7)$$

$$\frac{\partial X_i}{\partial \omega} \equiv -\int_0^\infty t_i s(t)\exp\left[-\sum_{i=1}^N (\mu_{ai} c t_i)\right]\cos\omega t\, dt \qquad (6.8)$$

$$\frac{\partial \ln A_i}{\partial \omega} \equiv -\frac{1}{A^2}\left(R\frac{\partial R_i}{\partial \omega} + X\frac{\partial X_i}{\partial \omega}\right) \qquad (6.9)$$

$$\frac{\partial \phi_i}{\partial \omega} \equiv -\frac{1}{A^2}\left(R\frac{\partial X_i}{\partial \omega} - X\frac{\partial R_i}{\partial \omega}\right) \qquad (6.10)$$

$$R = R(\mu_a = 0) + c\sum_{i=1}^N \int_0^{\mu_{ai}} \frac{\partial X_i}{\partial \omega}d\mu_a \qquad (6.11)$$

$$X = X(\mu_a = 0) - c\sum_{i=1}^N \int_0^{\mu_{ai}} \frac{\partial R_i}{\partial \omega}d\mu_a \qquad (6.12)$$

$$\ln A = \ln A(\mu_a = 0) - c\sum_{i=1}^N \int_0^{\mu_{ai}} \frac{\partial \varphi_i}{\partial \omega}d\mu_a \qquad (6.13)$$

$$\phi = \phi(\mu_a = 0) + c\sum_{i=1}^N \int_0^{\mu_{ai}} \frac{\partial \ln A_i}{\partial \omega}d\mu_a \qquad (6.14)$$

The first term on the right side in each equation of Eqs (6.11) to (6.14) is a response on the assumption of no absorption, and the second term is a term dependent upon absorption.

As described above, there are four types of description methods represented by Eqs (6.7) to (6.10) in the PMS and it is thus possible to implement optical CT image reconstruction methods corresponding to the respective equations. On that occasion, their respective weight functions can be calculated using the values obtained by substituting $\mu_{ai}=\mu_v$ into Eqs (6.7) to (6.10) and using the relations of Eqs (6.11) to (6.14), in much the same manner as described previously.

The above detailed the preferred embodiments of the present invention, but it is noted that the present invention is by no means intended to be limited to the above embodiments.

INDUSTRIAL APPLICABILITY

As described above, the present invention has permitted the direct and quick calculation of the time-resolved path length li in voxel i by solving the forward problems for the imaginary medium assumed to have the same scattering characteristics and boundary conditions as the measured medium and be nonabsorbing, so that the calculation time became shorter than in the conventional calculation of forward problems with absorption. Further, the invention obviated the need for the conventional time-consuming forward problem calculation of varying the absorption coefficient of each voxel and repeatedly solving the forward problems by the number of times equal to the total number of voxels. Accordingly, the present invention has permitted the provision of the methods capable of quickly calculating the photon path distribution inside the scattering medium of the heterogeneous system like living tissue.

What is claimed is:

1. A method of calculating a photon path distribution inside a scattering medium, comprising:

a first step of dividing a measured medium being the scattering medium, into N (1≦N) voxels each having a predetermined size and assumed to have a uniform absorption distribution in a measurement wavelength region;

a second step of hypothesizing an imaginary medium that can be assumed to have the same shape, boundary conditions, and scattering distribution as the measured medium, having a uniform refractive index distribution, and be nonabsorbing, for the measured medium divided into the N voxels;

a third step of setting a light injection position for injection of impulse light, and a light detection position for detection of an impulse response s(t) at a time t of the impulse light having been injected at the light injection position and having propagated in the imaginary medium, on a surface of the imaginary medium;

a fourth step of calculating the impulse response s(t) detected at the light detection position after injection of the impulse light at the light injection position into the imaginary medium;

a fifth step of calculating a photon existence probability density $Ui(t',t)$ that an ensemble of photons constituting the impulse response s(t) detected at the time t at the light detection position after injection of the impulse light at the light injection position into the imaginary medium has existed in an arbitrary voxel i (i=1, 2, . . . , N; 1≦N) in the imaginary medium at a time t' (0≦≦t) before the detection at the light detection position;

a sixth step of calculating a photon existence cumulative probability $Ui(t)$ that the ensemble of photons constituting the impulse response s(t) detected at the time t at the light detection position has existed in said voxel i, using the photon existence probability density $Ui(t',t)$; and a seventh step of calculating a time-resolved path length li in the voxel i, using the photon existence cumulative probability $Ui(t)$ and the impulse response s(t).

2. The method according to claim 1, further comprising, subsequent to the seventh step, an eighth step of calculating a weighted mean Li for time of the time-resolved path length li calculated for each arbitrary voxel i of the imaginary medium.

3. The method according to claim 1, further comprising, subsequent to the seventh step, an eighth step of calculating a weight function Wi corresponding to a predetermined measuring method for quantitatively measuring a concentration distribution of an absorptive constituent inside said measured medium, using said time-resolved path length li calculated for each arbitrary voxel i of the imaginary medium.

4. A method of calculating a photon path distribution inside a scattering medium, comprising:

a first step of dividing a measured medium being the scattering medium, into N (1≦N) voxels each having a predetermined size and assumed to have a uniform absorption distribution in a measurement wavelength region;

a second step of hypothesizing an imaginary medium that can be assumed to have the same shape, boundary conditions, and scattering distribution as the measured medium, have a uniform refractive index distribution, and be nonabsorbing, for the measured medium divided into the N voxels;

a third step of setting a light injection position for injection of impulse light, and a light detection position for detection of an impulse response s(t) at a time t of the impulse light having been injected at the light injection position and having propagated in the imaginary medium, on a surface of the imaginary medium;

a fourth step of calculating a photon existence probability density $Ui(t',t)$ that an ensemble of photons constituting the impulse response s(t) detected at the time t at the light detection position after injection of the impulse light at the light injection position into the imaginary medium has existed in an arbitrary voxel i (i=1, 2, . . . , N; 1≦N) in the imaginary medium at a time t' (0≦t'≦t) before the detection at the light detection position;

a fifth step of calculating a photon existence cumulative probability $Ui(t)$ that the ensemble of photons constituting the impulse response s(t) detected at the time t at the light detection position has existed in said voxel i, using the photon existence probability density $Ui(t',t)$;

a sixth step of calculating a sum $U(t)$ of said photon existence cumulative probabilities $Ui(t)$ for all the voxels; and a seventh step of calculating a time-resolved path length li in the voxel i, using the photon existence cumulative probability $Ui(t)$ and the sum $U(t)$ of the photon existence cumulative probabilities $Ui(t)$ for all the voxels.

5. The method according to claim 4, further comprising, subsequent to the seventh step, an eighth step of calculating a weighted mean Li for time of the time-resolved path length li calculated for each arbitrary voxel i of the imaginary medium.

6. The method according to claim 4, further comprising, subsequent to the seventh step, an eighth step of calculating a weight function Wi corresponding to a predetermined measuring method for quantitatively measuring a concentration distribution of an absorptive constituent inside said measured medium, using said time-resolved path length li calculated for each arbitrary voxel i of the imaginary medium.

\* \* \* \* \*